US012601016B2

(12) United States Patent
Chang et al.

(10) Patent No.: US 12,601,016 B2
(45) Date of Patent: Apr. 14, 2026

(54) GENETICALLY ENCODED FLUORESCENT INDICATORS UNDER OPTOGENETIC CONTROL AND USES THEREOF

(71) Applicants: LUMISTAR BIOTECHNOLOGY, INC., Taipei (TW); THE GOVERNORS OF THE UNIVERSITY OF ALBERTA, Edmonton (CA)

(72) Inventors: Yu-fen Chang, Taipei (TW); Yi Shen, Edmonton (CA); Yong Qian, Edmonton (CA); Min-wen Chung, Taipei (TW); Robert Campbell, Edmonton (CA)

(73) Assignees: LUMISTAR BIOTECHNOLOGY, INC., Taipei City (TW); THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 1015 days.

(21) Appl. No.: 17/289,946

(22) PCT Filed: Oct. 31, 2019

(86) PCT No.: PCT/CA2019/051550
§ 371 (c)(1),
(2) Date: Apr. 29, 2021

(87) PCT Pub. No.: WO2020/087178
PCT Pub. Date: May 7, 2020

(65) Prior Publication Data

US 2022/0017976 A1 Jan. 20, 2022

Related U.S. Application Data

(60) Provisional application No. 62/753,121, filed on Oct. 31, 2018.

(51) Int. Cl.
*C12Q 1/6897* (2018.01)
*G01N 21/64* (2006.01)

(52) U.S. Cl.
CPC ....... *C12Q 1/6897* (2013.01); *G01N 21/6428* (2013.01)

(58) Field of Classification Search
None
See application file for complete search history.

(56) References Cited

U.S. PATENT DOCUMENTS

| | | | | |
|---|---|---|---|---|
| 5,840,544 | A | 11/1998 | Hawkins et al. | |
| 2016/0176931 | A1* | 6/2016 | Kim ....................... | C07K 14/00 435/367 |

OTHER PUBLICATIONS

Shen et al., bioRxiv 213082; doi: https://doi.org/10.1101/213082, Nov. 2017, 59 pages (Year: 2017).*
Shen et al., Communications Biology 2:18, Jan. 2019, 10 pages (Year: 2019).*
Molina et al., Biophysical Journal 116:1873-1886, May 2019 (Year: 2019).*
Molina et al., bioRxiv 435891; doi: https://doi.org/10.1101/435891; Oct. 4, 2018 (Year: 2018).*
Piatkevich et al., Appl. Sci. 9:562, Feb. 2019 (Year: 2019).*
Greenwald et al., Chem. Rev. 118:11707-11794, Dec. 2018 (Year: 2018).*
Schreiter, E.R., Protein Data Bank Accession No. 5UKG, released Feb. 2018 (Year: 2018).*
Zhao, Y. et al., “An expanded palette of genetically encoded Ca2+ indicators”. Science, Sep. 30, 2011 (Sep. 30, 2011), vol. 333(6051), pp. 1888-1891, ISSN 1095-9203.
Higgins and Sharp, “Fast and sensitive multiple sequence alignments on a microcomputer” Cabios Communications. 5:151-153 (1989).
Higgins, D. G. et al. “Clustal V: improved software for multiple sequence alignment.” CABIOS 8:189-191. (1992).
Wu, J. et al. Improved orange and red Ca2+ indicators and photophysical considerations for optogenetic applications. ACS Chem. Neurosci., 2013, 4 (6), pp. 963-972. DOI: 10.1021/cn400012b.
Shen, Y. et al., “A genetically encoded Ca2+ indicator based on circularly permutated sea anemone red fluorescent protein eqFP578”. BMC Biology, Jan. 16, 2018 (Jan. 16, 2018), vol. 16:9, pp. 1-16, ISSN 1741-7007.
Qian, Y. et al., “A genetically encoded near-infrared fluorescent calcium ion indicator”. Nature Methods, Feb. 1, 2019 (Feb. 1, 2019), vol. 16, pp. 171-174, ISSN 1548-7091.

* cited by examiner

*Primary Examiner* — David Steadman
(74) *Attorney, Agent, or Firm* — Whiteford, Taylor & Preston, LLP; Peter J. Davis

(57) ABSTRACT

Disclosed are methods and compositions for real-time monitoring cellular calcium ion dynamics by red-shifted genetically encoded indicators under optogenetic control, in which millisecond-timescale of temporal control of optical activation or inactivation and signal recording can be achieved. The methods include artifact-free functional imaging in conjunction with optogenetic tools for studying cellular physiology, signal transduction and neuronal activity. Thus, all-optical and non-invasive approaches for drug screening, toxicity testing and assessment of cell functions may be provided.

6 Claims, 6 Drawing Sheets

Specification includes a Sequence Listing.

GENETICALLY ENCODED FLUORESCENT INDICATORS UNDER OPTOGENETIC CONTROL AND USES THEREOF

FIELD OF THE INVENTION

The present invention relates to methods and compositions related to artifact-free all-optical characterization of cellular physiology, which may be used for drug screening, toxicity testing and assessment of cell functions.

BACKGROUND

The calcium ion ($Ca^{2+}$) is a versatile second messenger, playing an essential role in all aspects of physiology and controlling key cell fate decisions, especially in excitable cells, such as cardiomyocytes, neurons and so on. Thus, the kinetics and spatial properties of $Ca^{2+}$ signals in cellular or subcellular compartments can reveal physiological response of cells to external stimuli for interrogation.

The use of genetically encoded $Ca^{2+}$ indicators (GECIs) has proven to be an indispensable tool for studying the spatio-temporal dynamics of cellular $Ca^{2+}$ signals in vivo and in vitro. They have been adopted as chronic probes for simultaneously monitoring neuronal activity in contexts ranging from dissociated neurons in vitro to brain activity in behaving animals. Numerous examples of imaging calcium transients in other cell types, such as cardiomyocytes and pancreatic beta cells, for studying $Ca^{2+}$-mediated signal transduction can also be found in literature.

Optogenetics is the combination of genetic and optical approaches, which can impose control with high spatial and temporal precision in a cell culture, cellular organelles, specific cells of living tissue and behaving animals. Combining an optogenetic actuator with a genetically encoded fluorescent indicator enables simultaneous manipulation and monitoring of dynamic changes of cellular physiology, signal transduction and neuronal activities. In this regard, the use of indicators with a red-shifted fluorescence spectra should be a better choice to work in pairs with commonly used opsin-based actuators, such as channelrhodopsin, as their excitation would not interfere with activation of such blue-light activated optogenetics. Moreover, indicators in this spectral range have a number of inherent benefits, such as reduction in tissue scattering, phototoxicity and back ground fluorescence, facilitating deeper imaging.

However, as widely recognized, red GECIs currently suffer from a number of limitations compared to the most highly optimized green GECIs (i.e., GCaMP6). These limitations include decreased sensitivity for RCaMP variants and complicated photophysics and lysosomal accumulation for R-GECO variants, especially the inherited property of undesirable blue-light activated photoswitching behavior that was also present in the DsRed-derived template (mApple) from which they were engineered. Such an artifact limits their use in conjunction with blue-light activated optogenetic actuators for all-optical stimulation and observation. While existing indicators with longer excitation and emission wavelengths falling within the near infrared (NIR) optical window (~650 nm to 900 nm) are ideal for in vivo imaging due to the minimum tissue scattering and absorption, the critical problem they have encountered is the dim fluorescence for qualified imaging acquisition.

This background information is provided simply to facilitate understanding of the invention described herein, and is not an admission that any particular art is prior art or is relevant.

SUMMARY OF THE INVENTION

The present invention relates generally to the use of genetically encoded $Ca^{2+}$ indicators (GECIs) such as K-GECO1, NIR-GECO1 and NIR-GECO2 for observation of calcium dynamics in cells. As such, aspects of the invention may include methods for assessment of drug efficacy, toxicity and cell functions under different conditions, enabling "pre-clinical trials" to be done in a dish, using a system as described herein.

Aspects of the invention may comprise the use of red-shifted GECIs in conjunction with optogenetic actuators for artifact-free all-optical stimulation and observation of calcium dynamics in cells. Embodiments of the invention are based on the use of optogenetic actuators which are activated by light having wavelengths which are significantly different from the wavelengths of light used to excite the GECIs.

Thus, in one aspect, the invention may comprise a method for examining the function of a cell, the method comprising:

(a) expressing a red-shifted genetically encoded $Ca^{2+}$ indicator (GECI) in the cell;

(b) obtaining an optical signal from the red-shifted GECI in response to a stimulation.

In another aspect, the invention may comprise a method for examining the function of a cell, the method comprising:

(a) expressing an optical actuator which is activated by light in the wavelength range of about 400 nm to about 570 nm, and a red-shifted genetically encoded $Ca^{2+}$ indicator (GECI) having an excitation wavelength greater than the activation wavelength of the optical actuator, in the cell;

(b) obtaining an optical signal from the red-shifted GECI in response to a stimulation imposed by the optical actuator caused by exposure to activation light.

BRIEF DESCRIPTION OF THE DRAWINGS

Features of the present invention may be described in the following detailed description that sets forth illustrative embodiments, in which the principles of the invention are utilized, and the accompanying drawings of which.

DETAILED DESCRIPTION

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular module, aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

The present invention provides methods and compositions for optical monitoring of a $Ca^{2+}$ signal using an entirely genetically encoded system expressing a red-shifted GECI. In some embodiments, the methods comprise expressing a blue or green light-activated optogenetic actuator in addition to a GECI in a cell or a cellular organelle, exposing the cell or cellular organelle to a light source for precise control of cell activity, preferably bidirectional control, i.e. activation or inhibition of a signaling pathway, and detecting the emitted fluorescence from the GECI. Intensity changes of the emitted fluorescence from the GECI reflects calcium ion dynamics. Such methods may allow real time monitoring of cellular calcium dynamics under precise control. Data interpretation is not interfered by any artifact of photoactivation, which may exist with many red GECIs. The method further allows monitoring calcium ion dynamics changes in response to external stimulus or stimuli. This is important not only for fundamental research about $Ca^{2+}$-dependent cellular activities but also, for example, for screening candidate agents for their capacity to affect cellular physiology, e.g., in drug screens and toxicity testing.

As used herein, "red-shifted GECI" means a GECI with an excitation wavelength greater than 500 nm and the peak of the emission spectrum greater than 550 nm. An "optogenetic actuator" means a genetically encoded, optically activated actuator, which embodies a combination of genetic and optical approach, and which can impose control optically (bidirectional control, i.e. activation or inhibition of a signaling pathway) with high spatial and temporal precision in a cell culture, cellular organelles, specific cells of living tissue and behaving animals.

Figure 1:
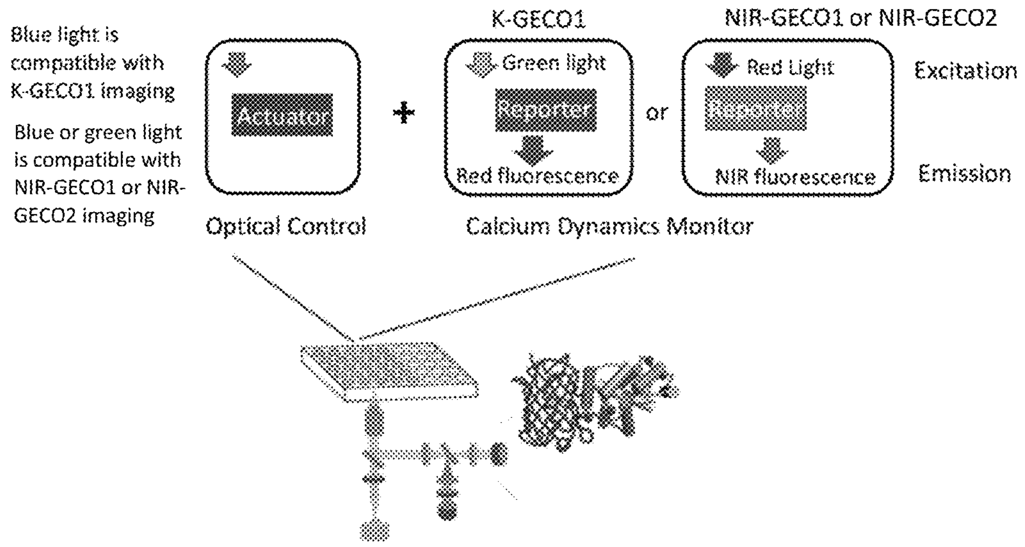
FIG. 1 shows a schematic representation of the combined use of optogenetic actuators and red-shifted GECIs for all-optical control and observation of cellular $Ca^{2+}$ dynamics.

FIG. 1 schematically depicts one embodiment of an all-genetically encoded system of the present invention. The system comprises a blue or green light-activated optogenetic actuator and a red-shifted GECI (such as K-GECO1, NIR-GECO1 and NIR-GECO2) for all-optical control and recording intracellular $Ca^{2+}$ transients.

In Vitro Properties of K-GECO1, NIR-GECO1 and NIR-GECO2

Figure 2:
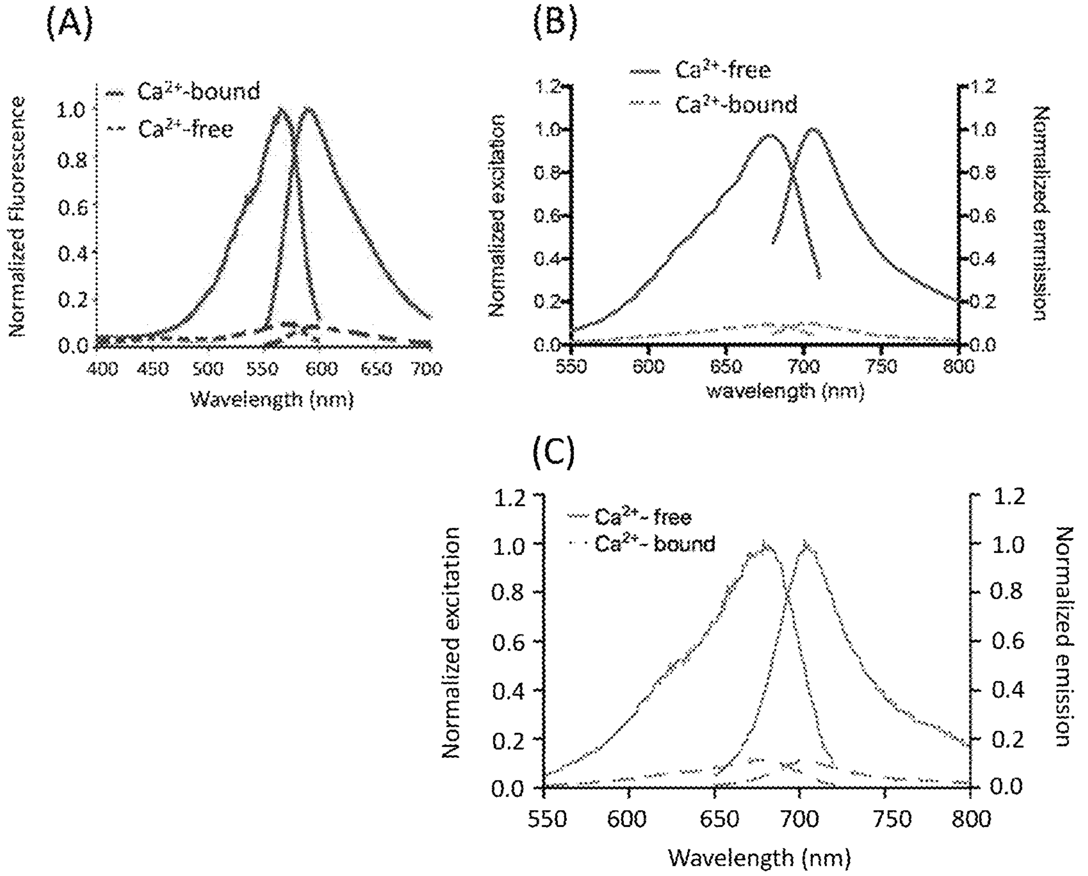
FIG. 2 shows fluorescence excitation and emission profiles of K-GECO1 (A), NIR-GECO1 (B) and NIR-GECO2 (C) in the presence and absence of $Ca^{2+}$.

The indicator, K-GECO1, is the archetype of a lineage of GECIs based on the red fluorescent protein (RFP) eqFP578 scaffold. It offers high sensitivity and fast kinetics, similar or better than those of current state-of-the-art indicators, with diminished lysosomal accumulation and negligible blue-light photoactivation in cultured cells. K-GECO1 is a monomeric red fluorescent indicator based on the RFP eqFP578 scaffold. In the $Ca^{2+}$-unbound state, the excitation and emission maxima of K-GECO1 are 568 and 594 nm, respectively. These two maxima are slightly blue-shifted to 565 and 590 nm in the $Ca^{2+}$-bound state, as shown in FIG. 2A. K-GECO1 exhibits a 12-fold fluorescent intensity increase upon $Ca^{2+}$ binding, with the extinction coefficient increasing from 19,000 to 61,000 $M^{-1}cm^{-1}$ and the quantum yield from 0.12 to 0.45. The fluorescence spectra characteristics and $Ca^{2+}$-induced fluorescence change of K-GECO1 are generally very similar to those of R-GECO1. However, K-GECO1 is about twofold brighter than R-GECO1 under one-photon excitation. $Ca^{2+}$ titration of purified K-GECO1 reveals that the protein has an apparent $K_d$ of 165 nM with a Hill coefficient of 1.12, similar to R-CaMP2 and other ckkap-based GECIs.

NIR-GECO1 is a near infrared indicator and is engineered from a naturally-monomeric infrared fluorescent proteins (mIFP). NIR-GECO1 has absorbance and emission peaks at 678 and 704 nm, respectively, and undergoes a 90% decrease in fluorescence intensity upon binding $Ca^{2+}$, serving as an inverse response indicator contrast to K-GECO1, as shown in FIG. 2B. $Ca^{2}$ titration of purified NIR-GECO1 reveals that the protein has an apparent $K_d$ of 215 nM with a Hill coefficient of 1.03. NIR-GECO2 shares 99% sequence identity and a similar spectral profile with that of NIR-GECO1, as shown in FIG. 2C. $Ca^{2+}$ titration of purified NIR-GECO2 reveals that the protein has an apparent $K_d$ of 480 nM with a Hill coefficient of 1.01.

Embodiments of the present invention comprise the use of a K-GECO1, NIR-GECO1 or NIR-GECO2 polypeptide, or combinations thereof, and substantially similar variants thereof. The polypeptides and substantially similar variants may be genetically encoded by the polynucleotide sequences disclosed herein, and substantially similar variants.

The amino acid sequences for K-GECO1, NIR-GECO1 and NIR-GECO2 are shown in Example 7 below.

Observing Cellular $Ca^{2+}$ Dynamics Under Precise Control by Optogenetic Actuators without Artifact Interference $Ca^{2+}$ serves as a critical messenger linking external stimuli to intracellular responses and regulates cell functions ranging from short-term muscle contraction and cell motility to long-term changes in gene expression and metabolism. The common external signals include neurotransmitters, hormones or growth factors. For excitable cells, the initial chemical stimulus may cause membrane depolarization or hyperpolarization, followed by activation or inhibition of a calcium-signaling pathway.

Conventionally, the impact of $Ca^{2+}$-dependent reactions in cells or cellular organelles was may be studied with pharmacological approaches, for instance, introducing chemical chelators to decrease intracellular $Ca^{2+}$ concentration. However, applying these reagents for modulation is irreversible and non-specific, and the kinetic profiles of $Ca^{2+}$ signals during the reactions are impeded. Recently developed optogenetic tools permit remote and non-invasive $Ca^{2+}$ signaling modulation, with excellent spatiotemporal resolution and rapid reversibility.

There are two types of optogenetic actuators for precise control of $Ca^{2+}$ signaling: (A) use of classical microbial opsin-based light-sensitive proteins which are able to depolarize or hyperpolarize the membrane potential in excitable cells; and (B) use of "genetically encoded $Ca^{2+}$ actuators" (GECAs), which are constructed by coupling photoreceptors (possessing photo-induced conformation change properties and are commonly derived from plants and bacteria), such as phytochrome, cryptochome, and LOV (light oxygen voltage)-based systems, with engineered proteins from receptor-operated $Ca^{2+}$ channels or store-operated $Ca^{2+}$ entry channels. Notable examples are OptoSTIM1 and Opto-CRAC engineered from calcium release-activated channels (CRAC), melanopsin and Opto-XRs engineered from G-protein coupled receptors, and Opto-RTKs relating to receptor tyrosine kinases.

Red-shifted GECIs are, in theory, most compatible with optogenetic actuators for simultaneous stimulation and imaging, as their excitation would not interfere with activation of commonly used blue light activated optogenetic proteins. However, most current red fluorescent proteins (RFPs) suffer from disadvantages, including low sensitivity, severe photoactivation interference and lysosomal accumulation. In particular, blue-light activated photo-switching behavior impedes their practical use in conjunction with optogenetic actuators for all-optical control and monitoring calcium dynamics. As for the genetically encoded reporters in the NIR range, currently available NIR GECIs suffer from the dim fluorescence for acquisition of qualified imaging.

In some embodiments, the combined use of K-GECO1, NIR-GECO1 and/or NIR-GECO2 and a type A optogenetic tool may provide artifact-free all-optical control and visualization of $Ca^{2+}$ changes in excitable cells in vivo or in vitro, in the absence or the presence of external stimuli, such as a drug candidate.

In other embodiments, the combined use of K-GECO1, NIR-GECO1 and/or NIR-GECO2 and a type B optogenetic tool mentioned above also provides the compatibility to work in pairs for all-optical control and monitoring $Ca^{2}$ dynamics in cell cultures (not limited to excitable cells only) in vivo or in vitro in the absence or the presence of external stimuli, such as a drug candidate.

Performance of K-GECO1 in Excitable Cells

In one aspect, K-GECO1 may provide visualization of changes in intracellular $Ca^{2+}$ levels in cardiomyocytes, neurons and pancreatic beta cells with or without precise optical control. In particular, human induced pluripotent stem cell (iPSC) derived cultures can serve as disease models for drug discovery, such as inherited heart disease, neurodegenerative disease and diabetes, and also for in vitro drug toxicity testing.

Figure 3:
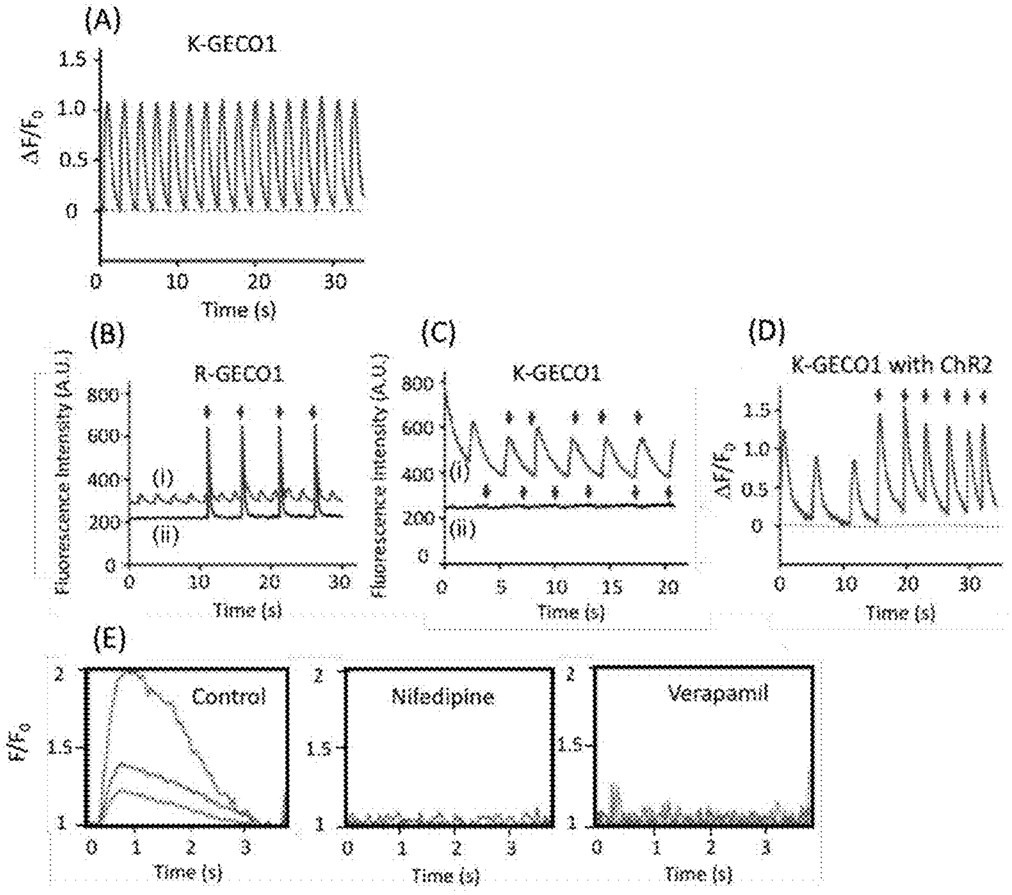
FIG. 3 shows the performance of K-GECO1 expressed in human induced pluripotent stem cell-derived cardiomyocytes (iPSC-CMs). (A) A representative time course of spontaneous $Ca^{2+}$ oscillations in iPSC-CMs as imaged using K-GECO1. (B) Photoactivation of R-GECO1 and (C) K-GECO1 in iPSC-CMs. Cells with and without spontaneous activities are shown in trace (i) and (ii), respectively. (D) Combined use of K-GECO1 and channelrhodopsin-2 (ChR2) in iPSC-CMs for all-optical control and observation of $Ca^{2+}$ transients. Illumination with 470-nm light at a pulse duration of 150 ms for optical control is indicated by arrowheads. (E) Small molecular inhibitors of the voltage-gated L-type calcium channels were applied to iPSC-CMs. iPSC-CMs were plated out at low density and exposed to clinically relevant doses of 100 nM and 1 μM for nifedipine and verapamil, respectively. Traces were obtained with optical stimulation by 470-nm light at a pulse duration of 40 ms at 0.3 Hz.

As shown in FIG. 3A, real-time monitor of spontaneous $Ca^{2+}$ oscillations in iPSC-CMs can be achieved using K-GECO1. FIGS. 3B and 3C show a comparison of photoactivation between R-GECO1 and K-GECO1 expressed in iPSC-CMs. Transfected cells (GECI only, no ChR2) were illuminated with 0.19 $W/cm^2$ of 470-nm LED light. Under these conditions, RGECO-1 exhibited a substantial photoactivation effect with a transient 200% increase in red fluorescence. Under the same illumination conditions, K-GECO1 had a negligible change in red fluorescence.

When iPSC-CMs were co-transfected with both K-GECO1 and ChR2, blue-light stimulation reliably induced $Ca^{2+}$ transients, demonstrating that the combination of K-GECO1 and ChR2 is feasible for all-optical excitation and imaging of iPSC-CMs, as may be seen in FIG. 3D.

The methods and compositions for all-optical manipulation and visualization of $Ca^{2+}$ dynamics in cell cultures of the present invention are feasible for examination of effects on cellular physiology imposed by external agents.

Application of voltage dependent L-type calcium channel inhibitors, verapamil (has off target hERG inhibition) and nifedipine, were tested at clinically relevant concentrations, and the results shown in FIG. 3E. Both calcium channel blockers suppress the triggered intensity change as imaged using K-GECO1, as expected.

In other embodiments, the combined use of K-GECO1 and ChR2 was applied to a classical neuronal cell model, PC12 cell line.

Figure 4:
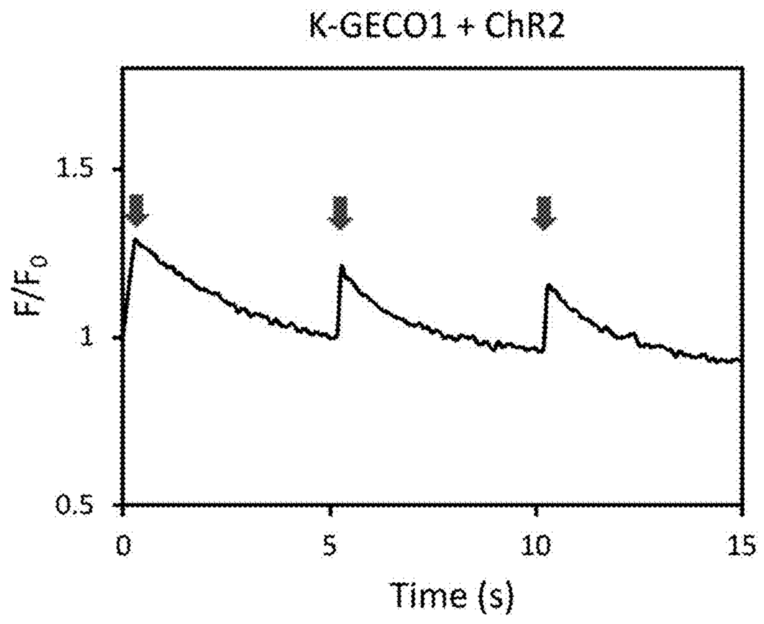
FIG. 4 shows a representative time course of $Ca^{2+}$ oscillations in a classical neuronal cell model, PC12 cell line, as imaged using K-GECO1 in conjunction with ChR2 for all-optical control and observation of $Ca^2$ transients. Illumination with 470-nm light at a pulse duration of 150 ms is indicated by arrowheads.

Blue-light stimulation reliably induced $Ca^{2+}$ transients in a PC12 cell line expressing both K-GECO1 and ChR2, demonstrating that the combination of K-GECO1 and ChR2 is feasible for all-optical excitation and imaging of neuronal-derived cells, as shown in FIG. 4.

As for other types of excitable cells, for example, pancreatic beta cells were also used in the present invention for testing. Generation of $Ca^{2+}$ transients by glucose-triggered voltage changes causes insulin release by exocytosis in the beta cells of the endocrine pancreas. Glucose causes ATP levels to rise, increasing the inhibition of an ATP dependent potassium channel $K_{ATP}$ reducing repolarisation, and causing calcium ions release. Augmentation of insulin release by chemical inhibition of $K_{ATP}$ using the sulphonylurea class of drugs has been a major Type II Diabetes management strategy. Since the insulin secretion can also be triggered by membrane depolarization directly above a certain threshold to fire an action potential, which results in increase of calcium influx through voltage-gated L-type $Ca^{2+}$ channels, some studies of the use of all-optical control and visualization of $Ca^{2+}$ transients in pancreatic beta cells have been reported. However, in these studies, underlying calcium dynamics were either interfered by photoactivation with blue light stimulation (for red GECIs), or drift upward as the excitation spectrum of the calcium indicators overlaps with the blue-green activation spectrum of the optical control tool causing unintended ChR2 activation during imaging.

Figure 5:
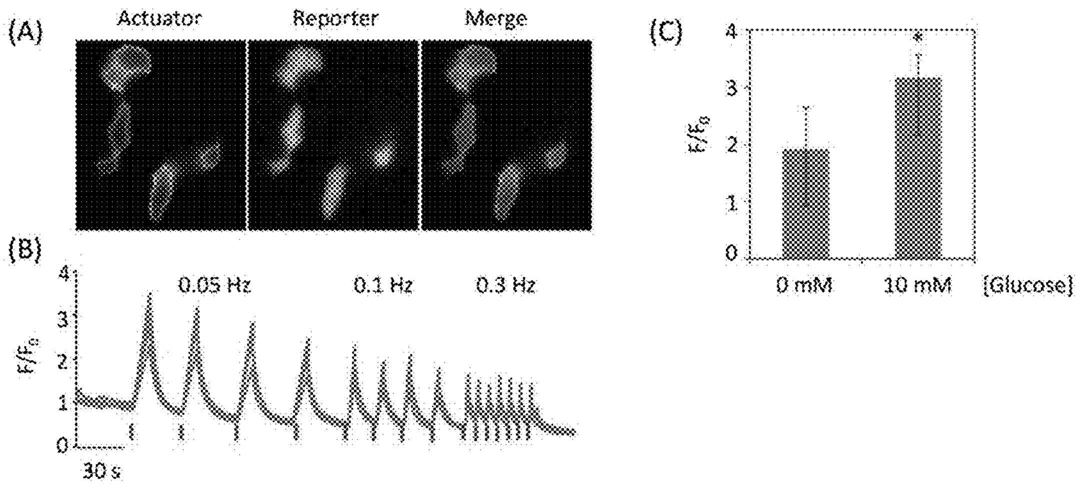
FIG. 5 shows the performance of K-GECO1 in conjunction with ChR2 in NIT-1 pancreatic β-cells. (A) NIT-1 pancreatic β-cells co-expressing K-GECO1 (shown in red) and ChR2-enhanced yellow fluorescent protein (EYFP) (shown in green). (B) Combined use of K-GECO1 and ChR2 in NIT-1 pancreatic β-cells for all-optical control and observation of $Ca^2$ transients. Representative time courses of $Ca^2$ oscillations by blue light (470 nm) stimulation at pulse durations of 10, 5 and 3 seconds for pacing at 0.05, 0.1 and 0.3 Hz, respectively, in the presence of 10 mM glucose. (C) Calcium influx upon optical stimulation at 0.05 Hz with or without glucose in NIT-1 cells. $F/F_0$ were analyzed from the first spike of the calcium intensity traces.

In one embodiment of the present invention, NIT-1 pancreatic beta cells may be used as a model for demonstration of the compatibility and performance of K-GECO1/NIR-GECO1 in combination with ChR2. In FIG. 5A, NIT-1 pancreatic beta cells expressing both K-GECO1 (shown in red) and ChR2-EYFP (shown in green) can be clearly seen under a microscope.

Blue-light stimulation induced $Ca^{2+}$ transients in the presence of 10 mM glucose at different pacing frequencies, as may be seen in FIG. 5B, demonstrating that the combination of K-GECO1 and ChR2 is feasible for all-optical excitation and imaging of NIT-1 cells.

Calcium ion dynamics changes in response to external stimuli of glucose concentrations can be imaged using K-GECO1 incorporated with ChR2. In the presence of 10 mM glucose, larger calcium influx was recorded as indicated by $F/F_0$, as shown in FIG. 5C.

Performance of K-GECO1 in Non-Excitable Cells

Figure 6:
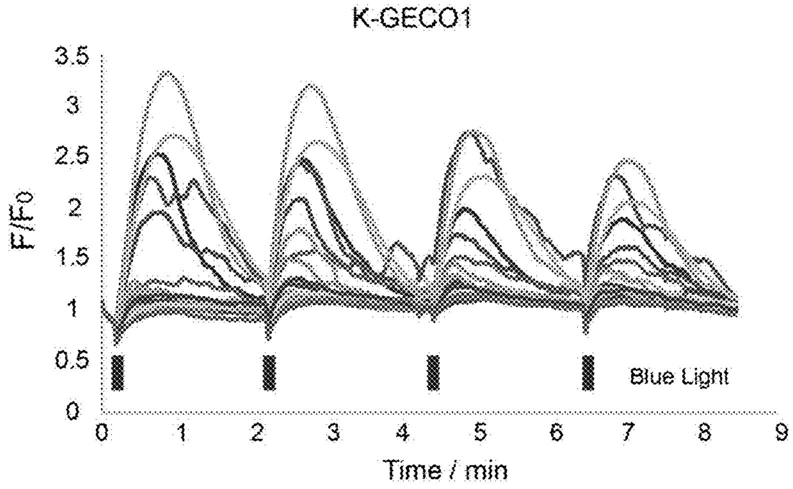
FIG. 6 shows the use of K-GECO1 in conjunction with Opto-CRAC actuator in HeLa cells. Increases in calcium transients can be observed upon blue light stimulation. Grey bars indicate 470 nm blue light stimulation on CRAC channels at a pulse duration of is.

Large calcium transients with duration up to 2 minutes were recorded in HeLa cells expressing Opto-CRAC-EYFP (type B optogenetic tools) and K-GECO1, as imaged using K-GECO1 after blue light stimulation and demonstrated in FIG. 6.

Performance of NIR-GECO1 and NIR-GECO2 in Excitable Cells

Figure 7:
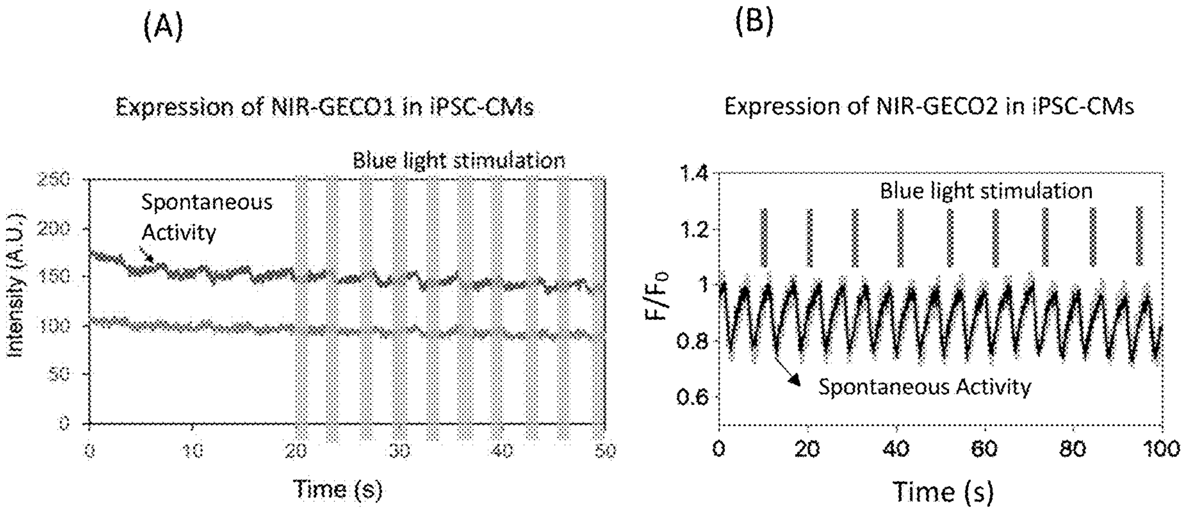
FIG. 7. Examination of photoactivation effects of NIR-GECO1 and NIR-GECO2 expressed in iPSC-CMs. (A) Representative time courses of $Ca^{2+}$ oscillations in iPSC-CMs as imaged using NIR-GECO1. Illumination with 470-nm LED light at 0.19 $W/cm^2$ light power with a pulse duration of 40 ms was indicated by pale-grey bars. Cells with spontaneous activity are colored in dark-grey and cells without spontaneous activity are colored in pale-grey. (B) Representative time courses of $Ca^{2+}$ oscillations as imaged using NIR-GECO2. Illumination with 470-nm LED light at 0.19 $W/cm^2$ light power with a pulse duration of 100 ms was indicated by grey bars.

NIR-GECO1 and NIR-GECO2 were expressed in iPSC-CMs for photoactivation testing as shown in FIGS. 7A and 7B, respectively. There are no significant changes in fluorescence intensity under illumination (0.19 $W/cm^2$ of 470-nm LED light indicated by grey bars at a pulse duration of 40 and 100 ms for NIR-GECO1 and NIR-GECO2 testing, respectively), suggesting that both NIR-GECO1 and NIR-GECO2 show negligible blue light-activated photoactivation behavior when expressed in cultured cells.

NIR-GECO1 and NIR-GECO2 were then tested for its performance in cardiovascular research. In one aspect of the present invention, a cell culture of stable immortalized cell lines, known as the HL-1 cell line, derived from mouse atrial cardiomyocytes is used as a model.

Figure 8:
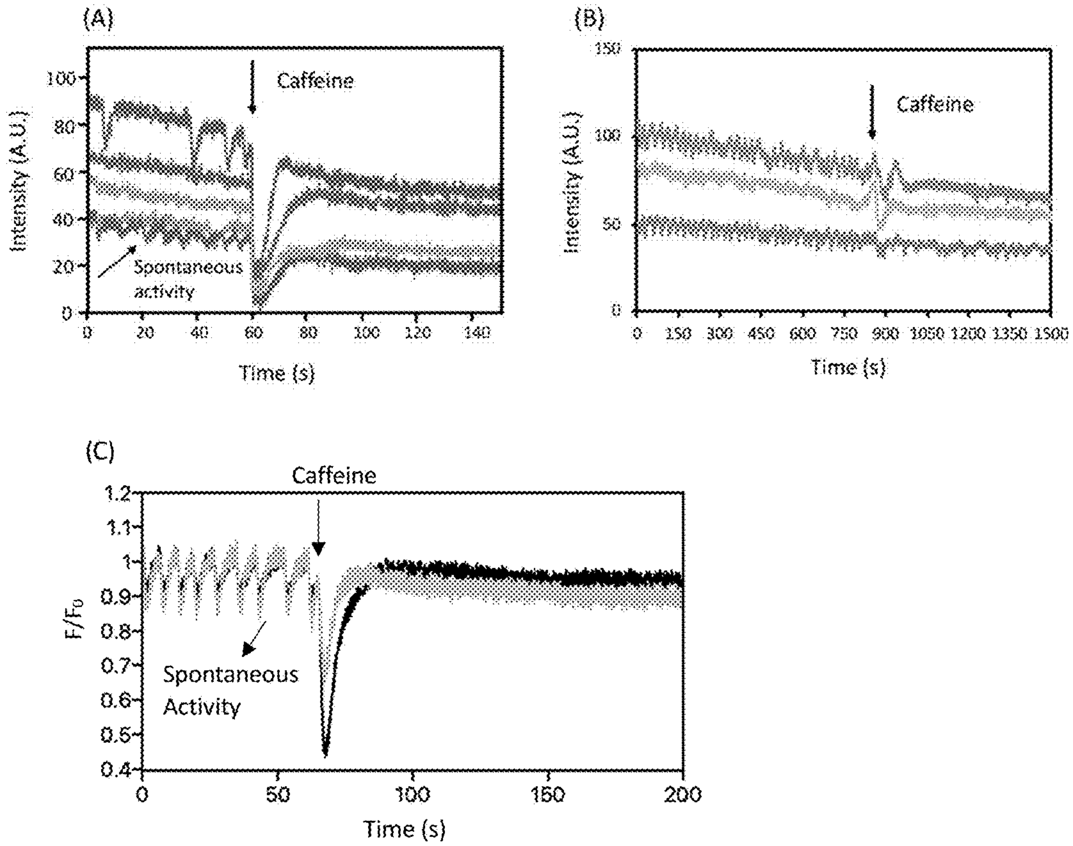
FIG. 8 shows the performance of NIR-GECO1 expressed in HL-1 cells (A) and iPSC-CMs (B), and of NIR-GECO2 expressed in iPSC-CMs (C). Representative time courses of $Ca^{2+}$ influx influenced by pharmacological stimulations of caffeine (10 mM). Spontaneous calcium oscillations were also able to be observed before applications of caffeine.

With reference to FIG. 8, NIR-GECO1 expressed in HL-1 (A) and iPSC-CMs (B), and NIR-GECO2 expressed in iPSC-CMs (C) were tested for pharmacological stimulation. After addition of 10 mM caffeine, significant decreases in fluorescence intensities were recorded, indicating increases in the cytosolic $Ca^{2+}$ concentration for both HL-1 and iPSC-CMs as imaged using NIR-GECO1 or NIR-GECO2.

Figure 9:
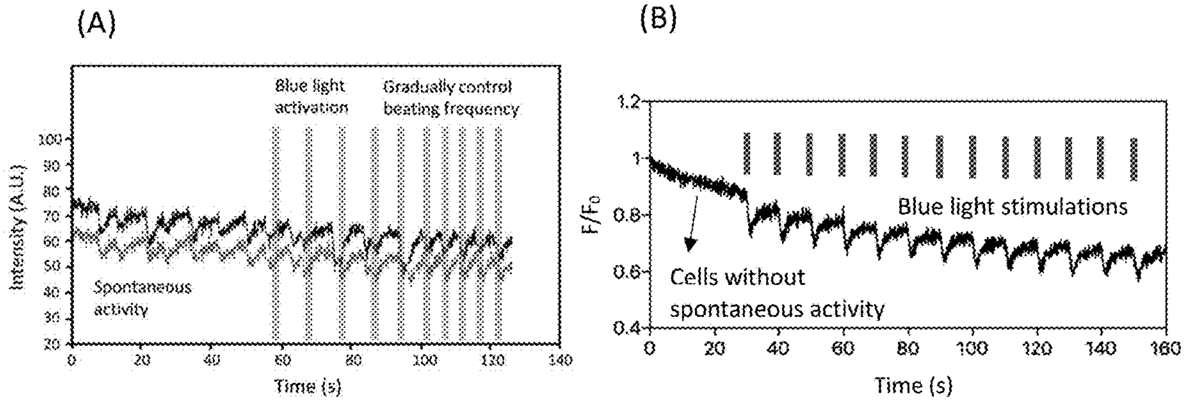
FIG. 9 shows representative time courses of $Ca^{2+}$ oscillations as imaged using NIR-GECO1 (A) and NIR-GECO2 (B) in conjunction with ChR2 actuator in iPSC-CMs. Optical controls with 470-nm LED light at a pulse duration of 150 and 100 ms for NIR-GECO1 and NIR-GECO2 respectively at different frequencies are indicated by grey bars.

With reference to FIG. 9, when NIR-GECO1 (A)/NIR-GECO2 (B) and ChR2 were co-expressed in the iPSC-CMs, $Ca^{2+}$ signals can be controlled by blue-light stimulation, demonstrating that the combined use of NIR-GECO1 or NIR-GECO2 and ChR2 is feasible for all-optical stimulation and imaging of $Ca^{2+}$ dynamics in iPSC-CMs.

Figure 10:
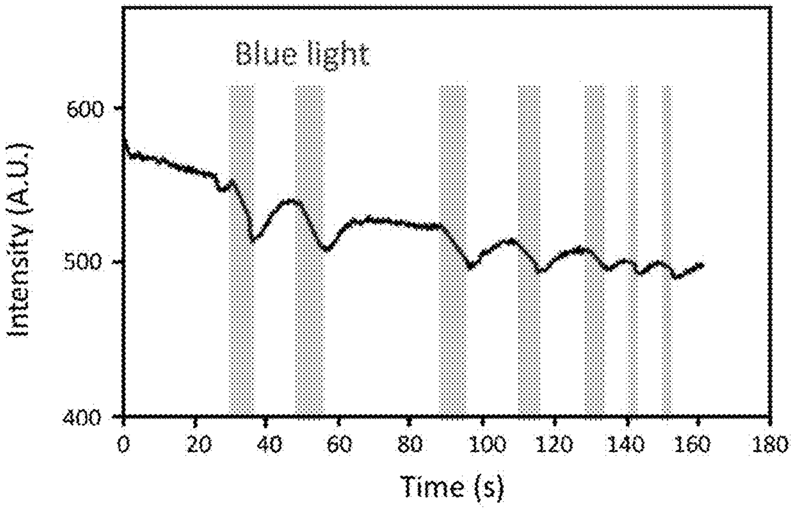
FIG. 10 shows a representative time course of $Ca^{2+}$ oscillations in NIT-1 pancreatic beta cells as imaged using NIR-GECO1 in conjunction with ChR2 actuator Optical stimulations by blue light (470 nm) at pulse durations of 10, 5, and 3 s for pacing are indicated by pale-grey bars.

With reference to FIG. 10, the performance of NIR-GECO1 in conjunction with ChR2 was also evaluated in NIT-1 pancreatic beta cells. Application of blue-light stimulation reliably induced $Ca^{2+}$ transients, showing its compatibility to work in pairs with a blue light-activated actuator.

Performance of NIR-GECO) and NIR-GECO2 in Non-Excitable Cells

Figure 11:
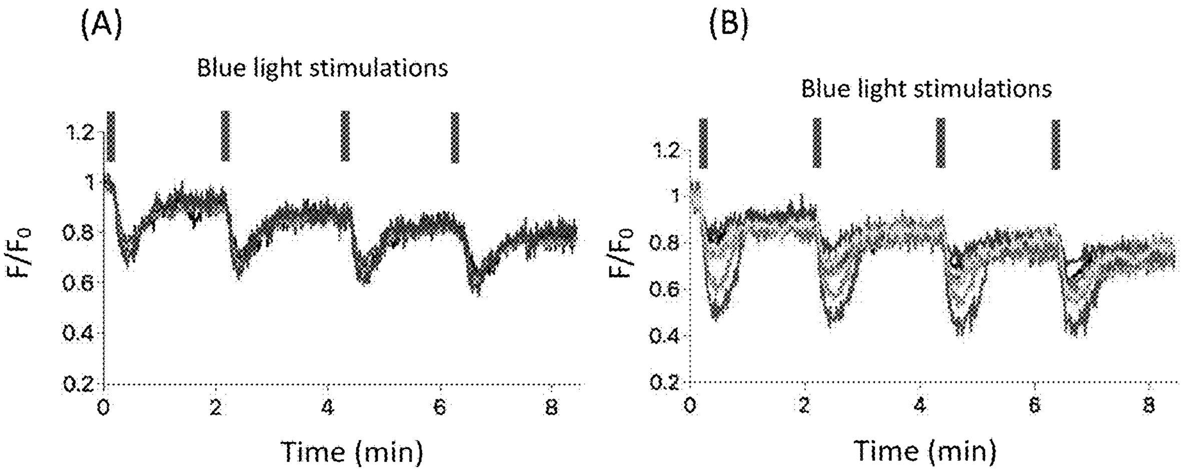
FIG. 11 shows representative time courses of provoked $Ca^{2+}$ transients as imaged using NIR-GECO1 (A) and NIR-GECO2 (B) activated by Opto-CRAC in HeLa cells. Grey bars indicate blue light stimulation (470 nm LED light) at a pulse duration of 1 s.

With reference to FIG. 11, for HeLa cells expressing Opto-CRAC-EYFP (a type B optogenetic tool) and NIR-GECO1 (A) and NIR-GECO2 (B), large calcium influxes were observed as imaged using NIR-GECO1/NIR-GECO2 after stimulating CRAC channel by 470-nm LED light at a pulse duration of 1 s. Grey bars indicate blue light stimulations.

EXAMPLES

Embodiments of the present invention are now described with reference to the following Examples. These Examples are provided for the purpose of illustration only.

Example 1: Plasmids for Mammalian Cell Imaging and Virus Production

ChR2-EYFP linked by a 2A peptide to K-GECO1 was amplified and subcloned into the pshuttle backbone for commercial adenoviral production (Vector Biolabs, Malvern, PA, US). All sequences are provided in Example 7.

Example 2: In Vitro Characterization

To purify K-GECO variants for in vitro characterization, the pBAD/His B plasmid encoding the variant of interest was used to transform electrocompetent *E. coli* DH10B cells and then plated on LB-agar plate with ampicillin (400 μg/mL). Single colonies were picked and inoculated into 5 mL LB medium supplemented with 100 g/mL ampicillin. Bacterial subcultures were incubated overnight at 37° C. Then, 5 mL of bacterial subculture was added into 500 mL of LB medium with 100 μg/mL of ampicillin. The cultures were incubated at 37° C. to an OD of 0.6. Following induction with L-arabinose to a final concentration of 0.02% (wt/vol), the cultures were then incubated at 20° C. overnight. Bacteria were harvested by centrifugation at 4000 g for 10 min, resuspended in 30 mM Tris-HCl buffer (pH 7.4), lysed using a French press, and then clarified by centrifugation at 13,000 g for 30 mins. Proteins were purified from the cell-free extract by Ni-NTA affinity chromatography (MCLAB).

The buffer of purified proteins was exchanged into 10 mM MOPS, 100 mM KCl, pH 7.2. Absorption spectra were recorded on a DU-800 UV-visible spectrophotometer (Beckman) and fluorescence spectra were recorded on a Safire2 fluorescence plate reader (Tecan). To determine the quantum yield, the fluorescent protein mCherry was used as a standard. The detailed protocol has been described previously in Campbell et al. *An expanded palette of genetically encoded $Ca^{2+}$ indicators. Science.* 2011 Sep. 30; 333(6051):1888-91. Briefly, the fluorescence emission spectra of each dilution of the protein solution of mCherry and K-GECO variants were recorded. The total fluorescence intensities were obtained by integration. The integrated fluorescence intensity versus absorbance was plotted for both mCherry and K-GECOs. The quantum yield was determined from the slopes of mCherry and K-GECOs. The extinction coefficient was determined by first measuring the absorption spectrum of K-GECO variants in a $Ca^{2+}$-free buffer and a $Ca^{2+}$-buffer. The absorption was measured following alkaline denaturation. The protein concentration was determined with the assumption that the denatured chromophore has an extinction coefficient of 44,000 M–1 cm–1 at 446 nm. The extinction coefficient of K-GECO variants was calculated by dividing the peak absorbance maximum by the concentration of protein.

For the $Ca^{2+}$ $K_d$ determination, the purified protein solution was diluted into a series of buffers, which were prepared by mixing $Ca^{2+}$-buffer and $Ca^{2+}$-free buffer with free $Ca^{2+}$ concentration in a range from 0 to 3900 nM. The fluorescence intensity of K-GECO variants in each solution was measured and subsequently plotted as a function of $Ca^{2+}$ concentration. The data were fitted to the Hill equation to obtain $K_d$ and the apparent Hill coefficient.

To purify NIR-GECO variants for in vitro characterization, the gene encoding variants of interest with a polyhistidine tag on the C terminus, was expressed from the pBAD vector. Bacteria were lysed with a cell disruptor (Constant Systems Ltd) and then centrifuged at 15,000 g for 30 min, and proteins were purified by Ni-NTA affinity chromatography (Agarose Bead Technologies). The buffer was typically exchanged to 10 mM MOPS, 100 mM KCl (pH 7.2) with centrifugal concentrators (GE Healthcare Life Sciences).

The extinction coefficients were determined by comparing the absorbance value at 678 nm to the absorbance value at the 391 nm and assuming an extinction coefficient of 39,900 $M^-$ $cm^-$ at 391 nm. For determination of quantum yields (Φ), purified mIFP (Φ=0.08) was used as a standard. The concentration of NIR-GECO variants ($Ca^{2+}$-free), NIR-GECO variants ($Ca^{2+}$-saturated) and mIFP was adjusted to have absorbance of 0.2-0.6 at 650 nm. A series of dilutions, with absorbance ranging from 0.01 to 0.05, were prepared, and integrated emission intensity versus absorbance was plotted. Quantum yields were determined from the slopes (S) of each line using the equation $\Phi_{protein} = \Phi_{standard} * (S_{protein}/S_{standard})$.

$Ca^{2+}$ titrations were carried out using EGTA-buffered $Ca^{2+}$ solutions (Calcium Calibration Buffer Kit no. 1, Life Technologies). We prepared buffers by mixing a CaEGTA buffer (30 mM MOPS, 100 mM KCl, 10 mM EGTA, 10 mM CaCl2) and an EGTA buffer (30 mM MOPS, 100 mM KCl, 10 mM EGTA) to give free $Ca^{2+}$ concentrations ranging from 0 to 39 μM at 25° C. Fluorescence intensities were plotted against $Ca^{2+}$ concentrations and fitted by a sigmoidal binding function to determine the Hill coefficient and $K_d$.

Example 3A: Cell Culture Conditions of HL-1 Cell Line

To culture the HL-1 cell line, flasks were pre-coated with gelatin/fibronectin at 37° C. overnight. Cells were cultured in supplemented Claycomb Medium (Claycomb Medium with 10% fetal bovine serum (Sigma Aldrich 12103C (Batch 8A0177)), 1 U/ml penicillin/streptomycin, 0.1 mM norepinephrine and 2 mM L-glutamine) and split 1:3 when they reached confluency.

Example 3B: Cell Culture Conditions of Human iPSC-Derived Cardiomyocytes

Human iPSC-derived cardiomyocytes (Human iPSC Cardiomyocytes—Male|ax2505) were purchased from Axol Bioscience. The cells were plated in two wells of a 6-well plate and cultured for eight days in Axol's Cardiomyocyte Maintenance Medium to 80-90% confluency. Cells then were re-plated on Fibronectin/Gelatin (0.5%/0.1%) coated glass bottom dishes for final observation with Tyrode's buffer.

Example 3C: Cell Culture Conditions of NIT-1 Pancreatic β-Cells

NIT-1 pancreatic β-cells were cultured in Ham's F12K medium with 2 mM L-glutamine and 2.5 g/L sodium bicarbonate. pH to 7.2. 10% heat inactivated FBS and a penicillin/streptomycin (all Invitrogen) was added to Ham's F12K medium every time when changing media. Cells were plated onto 35-mm glass-bottom dishes.

Example 3D: Cell Culture Conditions of PC12 Cells

PC12 cells were cultured in homemade 35-mm glass-bottom dishes in Dulbecco's modified Eagle medium (Sigma-Aldrich) containing 10% fetal bovine serum (Invitrogen) and 10% horse serum (BioWest).

Example 3E: Cell Culture Condition of HeLa Cells

HeLa cells were cultured in homemade 35-mm glass-bottom dishes in Dulbecco's modified Eagle medium (Sigma-Aldrich) containing 10% fetal bovine serum (Invitrogen).

Example 4: Transfection and Transduction

HL-1 Cells, iPSC-CMs and NIT-1 pancreatic β-cells were transfected with CMV-R-GECO1, pcDNA3.1-K-GECO1 or pcDNA3.1-NIR-GECO1 or pcDNA3.1-NIR-GECO2 and pcDNA3.1-hChR2-EYFP using transfection reagent of Lipofetamine 2000 (Invitrogen) (FIG. 3A-D, FIG. 5, 7-10). For PC12 cells (FIG. 4) and iPSC-CMs (FIG. 3E), viral transduction for 24 hours at an MOI of 5 preceded imaging by 2 days. HeLa cells were co-transfected with Opto-CRAC-EYFP and pcDNA3.1-K-GECO1 or pcDNA3.1-NIR-GECO1 or pcDNA3.1-NIR-GECO2 using transfection reagent of Lipofetamine 2000 (Invitrogen) (FIGS. 6 and 11).

Example 5: Optical Control and Calcium Imaging Using K-GECO1 and R-GECO1

An inverted microscope (D1, Zeiss) equipped with a 63× objective lens (NA 1.4, Zeiss) and a multiwavelength LED light source (pE-4000, CoolLED) was used. Blue (470 nm) and green (550 nm) excitation were used to illuminate ChR2-EYFP or Opto-CRAC-EYFP and K-GECO1 or R-GECO1, respectively. The GFP filter set (BP 470-490, T495lpxr dichroic mirror, and HQ525/50 emission filter) and the RFP filter set (HQ 545/30x, QS65lp dichroic mirror, and HQ620/60 emission filter) was used to confirm the expression of ChR2-EYFP and K-GECO1 or R-GECO1 in iPSC-CMs. The filter set (Q565lp dichroic mirror, and HQ620/60 emission filter) was used to stimulate ChR2 and to acquire fluorescence imaging of K-GECO1 or R-GECO1. Optical stimulation was achieved with the 470 nm LED light at 1.9 mW/mm$^2$ light power. Fluorescence signals were recorded using a CMOS camera (ORCA-Flash4.0LT, HAMAMATSU) controlled by a HC Image software.

Example 6: Optical Control and Calcium Imaging Using NIR-GECO1 and NIR-GECO2

An inverted microscope (D1, Zeiss) equipped with a 63× objective lens (NA 1.4, Zeiss) and a multiwavelength LED light source (pE-4000, CoolLED) was used. Blue (470 nm) and red (635 nm) excitation were used to illuminate ChR2-EYFP or Opto-CRAC-EYFP and NIR-GECO1, respectively. The GFP filter set (BP 470-490, T495lpxr dichroic mirror, and HQ525/50 emission filter) and the NIR filter set (ET 650/45x, T685lpxr dichroic mirror, and ET720/60 emission filter) was used to confirm the expression of ChR2-EYFP and NIR-GECO1 in iPSC-CMs. The filter set (T685lpxr dichroic mirror, and ET720/60 emission filter) was used to stimulate ChR2 and to acquire fluorescence imaging of NIR-GECO1. Optical stimulation was achieved with the 470 nm LED light at a power density of 1.9 mW/mm$^2$. Fluorescence signals were recorded by a CMOS camera (ORCA-Flash4.0LT, HAMAMATSU) and controlled by a HC Image software.

Example 7: Sequences

Nucleotide sequence encoding K-GECO1

(SEQ ID NO. 1)

ATGGGCAGCGTGAAGCTGATCCCCAGCCTGACCACCGTGATCCTCGTGAAGTCCATGCTGCG
GAAGCGGAGCTTCGGCAACCCCTTCAAGTATAATACGGAGACCCTGTACCCCGCTGACGGC
GGCCTGGAAGGCGCATGTGACATGGCCCTGAAGCTCGTGGGCGGGGGCCACCTGAACTGCA
GCCTTGAGACCACATACAGATCCAAGAAACCCGCTACGAACCTCAAGATGCCCGGTGTCTAC
AACGTGGACCACAGACTGGAACGAATCAAAGAGGCCGACGATGAGACCTACGTCGAGCTGC
ACGAGGTGGCTGTGGCCAGATACGTGGGCCTGGGTGGTGGCGGAGGTACAGGCGGGAGTGT
GAGCGAGCTGATTAAGGAGAACATGCCAATGAAGCTGTACATGGAGGGCACCGTGAACAAC
CACCACTTCAAGTGCACATCCGAGGGCGAAGGCAAGCCCTACGAGGGCACCCAGACCATGA
GAATCAAGGTCGTCGAGGGCGGCCCTCTCCCCTTCGCCTTCGACATCCTGGCTACCAGCTTC
ATGTACGGCAGCAGAACCTTCATCAAGCACCCTCCTGGCATCCCCGACTTCTTTAAGCAGTC
CTTCCCTGAGGGCTTCACATGGGAGAGAGTCACCACATACGAAGACGGGGGCGTGCTGACC
GCTACCCAGGACACCAGCCTCCAGGACGGCTGCCTCATCTACAACGTCAAGGTTAGAGGGA
TGAACTTCCCAGCCAACGGCCCTGTGATGCAGAAGAAAACACTCGGCTGGGAGGCCAGTAA
TGGCCAACTGACTGAAGAGCAGATCGCAGAATTTAAAGAGGCTTTCTCCCTATTTGACAAGG
ACGGGGATGGGACGATAACAACCAAGGAGCTGGGGACGGTGATGCGGTCTCTGGGGCAGA
ACCCCACAGAAGCGGAGCTGCAGGACATGATCAATGAAGTAGATGCCGACGGTGACGGCAC
ATTCGACTTCCCTGAGTTCCTGACGATGATGGCAAGAAAAATGAGTTATAGAGTCACTGAAG
AGGAAATTAGAGAAGCGTTCCGCGTGTTTGATAAGGACGGCAATGGCTACATCGGCGCAGC
AGAGCTTCGCCACGTGATGACAGACCTTGGAGAGAAGTTAACAGATGAGGAGGTTGATGAA
ATGATCAGGGTAGCAGACATCGATGGGGATGGTCAGGTAAACTACGAAGAGTTTGTACAAA
TGATGACAGCGAAGTAG

Nucleotide Sequence encoding ChR2-EYFP-2AP-K-GECO1

(SEQ ID NO. 2)

atggactatggcggcgctttgtctgccgtcggacgcgaacttttgttcgttactaatcctgtggtggtgaacgggtccgtcctggtccctgaggatcaatgtt
actgtgccggatggattgaatctcgcggcacgaacggcgctcagaccgcgtcaaatgtcctgcagtggcttgcagcaggattcagcattttgctgctgat
gttctatgcctaccaaacctggaaatctacatgcggctgggaggagatctatgtgtgcgc-
cattgaaatggttaaggtgattctcgagttctttttttgagtttaa
gaatccctctatgctctaccttgccacaggacaccgggtgcagtggctgcgctatgcagagtggctgctcacttgtcctgtcatccttatccacctgagcaa
cctcaccggcctgagcaacgactacagcaggagaaccatgggactccttgtctcagacatcgggactatcgtgtgggggctaccagcgccatggcaa
ccggctatgttaaagtcatcttcttttgtcttggattgtgctatggcgcgaacacat-
tttttcacgccgccaaagcatatatcgagggttatcatactgtgccaaa
gggtcggtgccgccaggtcgtgaccggcatggcatggctgtttttcgtgagctggggtatgttcccaattctcttcattttggggcccgaaggttttggcgtc
ctgagcgtctatggctccaccgtaggtcacacgattattgatctgatgagtaaaaattgttgggggttgttgggacactacctgcgcgtcctgatccacgag
cacatattgattcacggagatatccgcaaaaccaccaaactgaacatcggcggaacggagatcgaggtcgagactctcgtcgaagacgaagccgagg
ccggagccgtgccagcggccgccaccatggtgagcaagggcgaggagctgttcaccggggtggtgcccatcctggtcgagctggacggcgacgta
aacggccacaagttcagcgtgtccggcgagggcgagggcgatgccacctacggcaagctgaccctgaagttcatctgcaccaccggcaagctgccc
gtgccctggcccaccctcgtgaccaccttcggctacggcctgcagtgcttcgcccgctaccccgaccacatgaagcagcacgacttcttcaagtccgcc
atgcccgaaggctacgtccaggagcgcaccatcttcttcaaggacgacggcaactacaagacccgcgccgaggtgaagttcgagggcgacaccctgg
tgaaccgcatcgagctgaagggcatcgacttcaaggaggacggcaacatcctggggcacaagctggagtacaactacaacagccacaacgtctatatc
atggccgacaagcagaagaacggcatcaaggtgaacttcaagatccgccacaacatcgaggacggcagcgtgcagctcgccgaccactaccagcag
aacacccccatcggcgacggccccgtgctgctgcccgacaaccactacctgagctaccagtccgccctgagcaaagaccccaacgagaagcgcgat
cacatggtcctgctggagttcgtgaccgccgccgggatcactctcggcatggacgagctgtacaagggatccggagctactaacttcagcctgctgaag
caggctggagacgtggaggagaaccctggacctactagtatgggcagcgtgaagctgatccccagcctgaccaccgtgatcctcgtgaagtccatgct
gcggaagcggagcttcggcaaccccttcaagtataatacggagaccctgtaccccgctgacggcggcctggaaggcgcatgtgacatggccctgaag
ctcgtgggcgggggccacctgaactgcagccttgagaccacatacagatccaagaaacccgctacgaacctcaagatgcccggtgtctacaacgtgga
ccacagactggaacgaatcaaagaggccgacgatgagacctacgtcgagctgcacgaggtggctgtggccagatacgtgggcctgggtggtggcgg
aggtacaggcgggagtgtgagcgagctgattaaggagaacatgccaatgaagctgtacatggagggcaccgtgaacaaccaccacttcaagtgcacat
ccgagggcgaaggcaagccctacgagggcacccagaccatgagaatcaaggtcgtcgagggcggccctctccccttcgccttcgacatcctggctac
cagcttcatgtacggcagcagaaccttcatcaagcaccctcctggcatccccgacttctttaagcagtccttccctgagggcttcacatgggagagagtca
ccacatacgaagacgggggcgtgctgaccgctacccaggacaccagcctccaggacggctgcctcatctacaacgtcaaggttagagggatgaacttc
ccagccaacggccctgtgatgcagaagaaaacactcggctgggaggccagtaatggccaactgactgaagagcagatcgcagaatttaaagaggcttt
ctccctatttgacaaggacggggatgggacgataacaaccaaggagctggggacggtgatgcggtctctggggcagaaccccacagaagcggagct
gcaggacatgatcaatgaagtagatgccgacggtgacggcacattcgacttccctgagttcctgacgatgatggcaagaaaaatgagttatagagtcact
gaagaggaaattagagaagcgttccgcgtgtttgataaggacggcaatggctacatcggcgcagcagagcttcgccacgtgatgacagaccttggaga
gaagttaacagatgaggaggttgatgaaatgatcagggtagcagacatcgatggggatggtcaggtaaactacgaagagtttgtacaaatgatgacagc
gaagtag (The grey highlighted portion is K-GECO1)

Nucleotide Sequence encoding NIR-GECO1

(SEQ ID NO. 3)

ATGTCGGTACCGCTGACTACCTCAGCATTCGGCCACGCGTTTCTGGCTAACTGTGAACGTGA
GCAGATCCACCTGGCGGGCTCCATTCAGCCGCACGGTATCCTGCTGGCTGTTAAAGAGCCTG
ACAACGTGGTGATCCAGGCTTCTATTAACGCTGCGGAGTTCCTGAACACCAACTTTGTTGTT

-continued

GGCCGTCCGCTGCGTGACCTGGGCGGCGATCTGCCTTTGCAGATCCTGCCGCACCTGAACGG
CCCGCTGCACCTGGCTCCGATGACCCTGCGTTGTACTGTGGGTTCTCCGCCGCGTCGTGTGGA
CTGTACCATTCATCGTCCGTCTAACGGCGGCCTGATCGTAGAACTGGAACCAGCAACCAAGG
CCACTAACATTGCGCCGGCTCTGGTCGGTGCGCTTCATCGTATCACTTCTTCATCCTCCCTGA
TGGGCCTGTGTGACGAAACCGCGACTATTTTCCGTGAGATTACTGGCTTCGACCGTGTGATG
GTAATGCGTCTCGGCGCGCTTGACGATCTGACTGAAGAGCAGATCGCAGAGATTAAAGAGG
CTTTCTCCCTATTTGACAAGGACGGGGACGGGACGATAACAACCAAGGAGCTGGGGACGGT
GTTCCGGTCTCTGGGGCAGAACCCCCACAGAAGCAGAGCTGCAGGACATGATCAATGAAGTA
GATGCCGATGGCGACGGCACATTCGACTTCCCTGAGTTCCTGACGATGATGGCAAGGAAAAT
GAATGACTCAGACAGTGAAGAGGAAATTAGAGAAGCGTTCCGCGTGTTTGATAAGGACGGC
AATGGCTACATCGGCGCAGCAGAGCTTCGCCACGTGATGACAGACCTTGGTGAGAAGTTAA
CTGATGAGGAGGTTGATGAAATGATCAGGGTAGCAGACAACGATGGGGATGGTCAGGTAAA
CTACGAAGAGTTTGTACAAATGATGACAGCGAAGGGTGGCGGAGGTTCTGTAGATTCATCA
CGTCGTAAGTGGAATAAGGCAGGTCACGCAGTCAGAGCTATAGGTCGGCTGAGCTCGCGTA
GGCATGATTTGCTGTCCGAATGTCGTCGTGCGGACCTGGAAGCGTTCCTGGGTAACCGCTAC
CCGGCGTCTACTATTCCGCAGATCGCTCGTCGCCTGTACGAACTTAACCGTGTTCGCCTGCTG
GTAGATGTGAACTATACTCCGGTTCCGCTACAGCCGCGCATCAGCCCGCTGAACGGTCGTGA
TCTGGATATGTCCCTGTCTTGCCTGCGCTCTATGTCCCCGATCCACCAGAAATACATGCAGGA
CATGGGCGTTGGCGCAACCCTGGTTTGCTCTCTGATGGTGTCTGGTCGTCTGTGGGGTCTGAT
CGTTTGCCACCACTACGAACCGCGCTTCGTTCCGTCCCACATTCGCGCTGCTGGCGAAGCGC
TGGCGGAAACTTGTGCGAACCGCATCGCGACGCTGGAGAGCTTTGCACAGTCTCAGTCCAAA
TGA

Nucleotide Sequence encoding NIR-GECO2

(SEQ ID NO. 4)

ATGTCGGTACCGCTGACTACCTCAGCATTCGGCCACGCGTTTCTGGCTAACTGTGAACGTGA
GCAGATCCACCTGGCGGGCTCCATTCAGCCGCACGGTATCCTGCTGGCTGTTAAAGAGCCTG
ACAACGTGGTGATCCAGGCTTCTATTAACGCTGCGGAGTTCCTGAACACCAACTTTGTTGTT
GGCCGTCCGCTGCGTGACCTGGGCGGCGATCTGCCTTTGCAGATCCTGCCGCACCTGAACGG
CCCGCTGCACCTGGCTCCGATGACCCTGCGTTGTACTGTGGGTTCTCCGCCGCGTCGTGTGGA
CTGTACCATTCATCGACCGTCTAACGGCGGCCTGATCGTAGAACTGGAACCAGCAACCAAGG
CCACTAACATTGCGCCGGCTCTGGTCGGTGCGCTTCATCGTATCACTTCTTCATCCTCCCTGA
TGGGCCTGTGTGACGAAACCGCGACTATTTTCCGTGAGATTACTGGTTTCGACCGTGTGATG
GTAATGCGTCTCGGCGCGCTTGACGATCTGACTGAAGAGCAGATCGCAGAGATTAAAGAGG
CTTTCTCCCTATTTGACAAGGACGGGGACGGGACGATAACAACCAAGGAGCTGGGGACGGT
GTTCCGGTCTCTGGGGCAGAACCCCCACAGAAGCAGAGCTGCAGGACATGATCAATGAAGTA
GATGCCGATGGCGACGGCATATTCGACTTCCCTGAGTTCCTGACGATGATGGCAAGGAAAAT
GAATGACTCAGACAGTGAAGAGGAAATTAGAGGAGCGTTCCGCGTGTTTGATAAGGACGGC
AATGGCTACATCGGCGCAGCAGAGCTTCGCCACGTGATGACAGACCTTGGTGAGAAGTTAA
CTGATGAGGAGGTTGATGAAATGATCAGGGTAGCAGACAACGATGGGGATGGTCAGGTAAA
CTACGAAGAGTTTGTACAAATGATGACAGCGAAGGGTGGCGGAGGTTCTGTAGATTCATCA
CGTCGTAAGTGGAATAAGGCAGGTCACGCAGTCAGAGCTATAGGTCGGCTGGGCTCGCGTA
GGCATGATTTGCTGTCCGAATGTCGTCGTGCGGACCTGGAAGCGTTCCTAGGTAACCGCTAC
CCGGCGTCTACTATTCCGCAGATCGCTCGTCGCCTGTACGAACTCAACCGTGTTCGCCTGCTG
GTAGATGTGAACTATACTCCGGTTCCGCTAGAGCCGCGCATCAGCCCGCTGAACGGTCGTGA
TCTGGATATGTCCCTGTCTTGCCTGCGCTCTATGTCCCCGATCCACCAGAAATACATGCAGGA
CATGGGCGTTGGCGCAACCCTGGTTTGCTCTCTGATGGTGTCTGGTCGTCTGTGGGGTCTGAT
CGTTTGCCACCACTACGAACCGCGCTACGTTCCGTCCCACATTCGCGCTGCTGGCGAAGCGC
TGGCGGAAGCATGTGCGAACCGCATCGCGACGCTGGAGAGCTTTGCACAGTCTCAGTCCAA
A

Amino Acid Sequence Of K-GECO1

(SEQ ID NO. 5)

MGSVKLIPSLTTVILVKSMLRKRSFGNPFKYNTETLYPADGGLEGACDMA
LKLVGGGHLNCSLETTYRSKKPATNLKMPGVYNVDHRLERIKEADDETYV
ELHEVAVARYVGLGGGGGTGGSVSELIKENMPMKLYMEGTVNNHHFKCTS
EGEGKPYEGTQTMRIKVVEGGPLPFAFDILATSFMYGSRTFIKHPPGIPD
FFKQSFPEGFTWERVTTYEDGGVLTATQDTSLQDGCLIYNVKVRGMNFPA
NGPVMQKKTLGWEASNGQLTEEQIAEFKEAFSLFDKDGDGTITTKELGTV
MRSLGQNPTEAELQDMINEVDADGDGTFDFPEFLTMMARKMSYRVTEEEI
REAFRVFDKDGNGYIGAAELRHVMTDLGEKLTDEEVDEMIRVADIDGDGQ
VNYEEFVQMMTAK

Amino Acid Sequence of NIR-GECO1

(SEQ ID NO. 6)

MSVPLTTSAFGHAFLANCEREQIHLAGSIQPHGILLAVKEPDNVVIQASI
NAAEFLNTNFVVGRPLRDLGGDLPLQILPHLNGPLHLAPMTLRCTVGSPP
RRVDCTIHRPSNGGLIVELEPATKATNIAPALVGALHRITSSSSLMGLCD
ETATIFREITGFDRVMVMRLGALDDLTEEQIAEIKEAFSLFDKDGDGTIT
TKELGTVFRSLGQNPTEAELQDMINEVDADGDGTFDFPEFLTMMARKMND
SDSEEEIREAFRVFDKDGNGYIGAAELRHVMTDLGEKLTDEEVDEMIRVA
DNDGDGQVNYEEFVQMMTAKGGGGSVDSSRRKWNKAGHAVRAIGRLSSRR
HDLLSECRRADLEAFLGNRYPASTIPQIARRLYELNRVRLLVDVNYTPVP
LQPRISPLNGRDLDMSLSCLRSMSPIHQKYMQDMGVGATLVCSLMVSGRL
WGLIVCHHYEPRFVPSHIRAAGEALAETCANRIATLESFAQSQSK

Amino Acid Sequence of NIR-GECO2

(SEQ ID NO. 7)

MSVPLTTSAFGHAFLANCEREQIHLAGSIQPHGILLAVKEPDNVVIQASI
NAAEFLNTNFVVGRPLRDLGGDLPLQILPHLNGPLHLAPMTLRCTVGSPP
RRVDCTIHRPSNGGLIVELEPATKATNIAPALVGALHRITSSSSLMGLCD
ETATIFREITGFDRVMVMRLGALDDLTEEQIAEIKEAFSLFDKDGDGTIT

-continued

```
TKELGTVFRSLGQNPTEAELQDMINEVDADGDGIFDFPEFLTMMARKMND
SDSEEEIRGAFRVFDKDGNGYIGAAELRHVMTDLGEKLTDEEVDEMIRVA
DNDGDGQVNYEEFVQMMTAKGGGGSVDSSRRKWNKAGHAVRAIGRLGSRR
HDLLSECRRADLEAFLGNRYPASTIPQIARRLYELNRVRLLVDVNYTPVP
LEPRISPLNGRDLDMSLSCLRSMSPIHQKYMQDMGVGATLVCSLMVSGRL
WGLIVCHHYEPRYVPSHIRAAGEALAEACANRIATLESFAQSQSK
```

Interpretation

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

The term "expression", as used herein, refers to the production of a functional end-product (e.g., a mRNA or a protein [either precursor or mature]).

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active protein. For example, the fragment or subfragment can be used in the design of chimeric genes to produce the desired phenotype in a transformed cell. Chimeric genes can be designed for use in suppression by linking a nucleic acid fragment or subfragment thereof, whether or not it encodes an active enzyme, in the sense or antisense orientation relative to a promoter sequence.

The term "substantially similar" refers to nucleic acids wherein changes in one or more nucleotide bases do not affect the ability of the nucleic acid to mediate gene expression or produce a certain phenotype. These terms also refer to modifications of the nucleic acids of the instant invention such as deletion or insertion of one or more nucleotides that do not substantially alter the functional properties of the resulting nucleic acid relative to the initial, unmodified nucleic acid. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth et al., Anal. Biochem. 138:267-284 (1984): $T_m$=81.5.degree. C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Interscience, New York (1995). Hybridization and/or wash conditions can be applied for at least 10, 30, 60, 90, 120, or 240 minutes.

Differences between presently disclosed polypeptides and substantially similar variants are limited so that the sequences of the former and the latter are closely similar overall and, in many regions, identical. They may differ in amino acid sequence by one or more substitutions, additions, deletions, fusions and truncations, which may be present in any combination. These differences may produce silent changes and result in a functionally equivalent polypeptide. Thus, it will be readily appreciated by those of skill in the art, that any of a variety of polynucleotide sequences is capable of encoding the polypeptides and variant polypeptides of the instant disclosure. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Sequence identity" or "identity" in the context of nucleic acid or polypeptide sequences refers to the nucleic acid bases or amino acid residues in two sequences that are the same when aligned for maximum correspondence over a specified comparison window. Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50% h, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp, CABIOS. 5:151-153 (1989); Higgins, D. G. et al. (1992) Comput. Appl. Biosci. 8:189-191) and found in the MegAlign™ program of the LASERGENE bioinformatics computing suite (DNASTAR Inc., Madison, Wis.). For multiple alignments, the default values correspond to GAP PENALTY-10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. "BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptide variants, wherein such polypeptide variants have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 90%, 91%, 92%, 93%, 94%, 95%, 96%, 97%, 98% or 99%.

The corresponding structures, materials, acts, and equivalents of all means or steps plus function elements in the claims appended to this specification are intended to include any structure, material, or act for performing the function in combination with other claimed elements as specifically claimed.

It is noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The invention claimed is:

1. A method for examining a function of a cell in a sample, the method comprising:

(a) expressing a red-shifted genetically encoded $Ca^{2+}$ indicator (GECI) comprising the amino acid sequence of SEQ ID NO: 5 in the cell;

(b) obtaining an optical signal from the red-shifted GECI in response to a stimulation; and (c) characterizing the sample by analyzing the optical signal responses in order to determine functional properties of the sample.

2. The method of claim 1, wherein the sample is a two- or three-dimensional (2D or 3D) cell culture, cellular organelles, stem cells or a mammalian blood plasma.

3. The method of claim 1, wherein the sample characterization step (c) comprises determining cell response to exposure to an agent.

4. The method of claim 1, wherein analyzing the optical signal responses comprises characterization of calcium influx of the sample.

5. The method of claim 1, wherein the cell is transformed or transfected with a nucleic acid encoding the red-shifted GECI.

6. The method of claim 5, wherein the nucleic acid has the nucleotide sequence of SEQ ID NO: 1 or SEQ ID NO: 2.

* * * * *

SEQUENCE LISTING

```
<160> NUMBER OF SEQ ID NOS: 7

<210> SEQ ID NO 1
<211> LENGTH: 1242
<212> TYPE: DNA
<213> ORGANISM: Artificial Sequence
<220> FEATURE:
<223> OTHER INFORMATION: Artificial sequence based on bacterial sequence

<400> SEQUENCE: 1

atgggcagcg tgaagctgat ccccagcctg accaccgtga tcctcgtgaa gtccatgctg      60

cggaagcgga gcttcggcaa ccccttcaag tataatacgg agaccctgta ccccgctgac     120

ggcggcctgg aaggcgcatg tgacatggcc ctgaagctcg tgggcggggg ccacctgaac     180

tgcagccttg agaccacata cagatccaag aaacccgcta cgaacctcaa gatgcccggt     240

gtctacaacg tggaccacag actggaacga atcaaagagg ccgacgatga gacctacgtc     300

gagctgcacg aggtggctgt ggccagatac gtgggcctgg gtggtggcgg aggtacaggc     360

gggagtgtga gcgagctgat taaggagaac atgccaatga agctgtacat ggagggcacc     420

gtgaacaacc accacttcaa gtgcacatcc gagggcgaag gcaagcccta cgagggcacc     480

cagaccatga gaatcaaggt cgtcgagggc ggccctctcc ccttcgcctt cgacatcctg     540

gctaccagct tcatgtacgg cagcagaacc ttcatcaagc accctcctgg catccccgac     600

ttctttaagc agtccttccc tgagggcttc acatgggaga gagtcaccac atacgaagac     660

gggggcgtgc tgaccgctac ccaggacacc agcctccagg acggctgcct catctacaac     720

gtcaaggtta gagggatgaa cttcccagcc aacggccctg tgatgcagaa gaaaacactc     780

ggctgggagg ccagtaatgg ccaactgact gaagagcaga tcgcagaatt taaagaggct     840

ttctccctat ttgacaagga cggggatggg acgataacaa ccaaggagct ggggacggtg     900

atgcggtctc tggggcagaa ccccacagaa gcggagctgc aggacatgat caatgaagta     960
```

-continued

```
gatgccgacg gtgacggcac attcgacttc cctgagttcc tgacgatgat ggcaagaaaa   1020

atgagttata gagtcactga agaggaaatt agagaagcgt tccgcgtgtt tgataaggac   1080

ggcaatggct acatcggcgc agcagagctt cgccacgtga tgacagacct tggagagaag   1140

ttaacagatg aggaggttga tgaaatgatc agggtagcag acatcgatgg ggatggtcag   1200

gtaaactacg aagagtttgt acaaatgatg acagcgaagt ag                      1242


<210> SEQ ID NO 2
<211> LENGTH: 2973
<212> TYPE: DNA
<213> ORGANISM: Artificial Sequence
<220> FEATURE:
<223> OTHER INFORMATION: Artificial sequence based on bacterial sequence

<400> SEQUENCE: 2

atggactatg gcggcgcttt gtctgccgtc ggacgcgaac ttttgttcgt tactaatcct     60

gtggtggtga acgggtccgt cctggtccct gaggatcaat gttactgtgc cggatggatt    120

gaatctcgcg gcacgaacgg cgctcagacc gcgtcaaatg tcctgcagtg gcttgcagca    180

ggattcagca ttttgctgct gatgttctat gcctaccaaa cctggaaatc tacatgcggc    240

tgggaggaga tctatgtgtg cgccattgaa atggttaagg tgattctcga gttctttttt    300

gagtttaaga atccctctat gctctacctt gccacaggac accgggtgca gtggctgcgc    360

tatgcagagt ggctgctcac ttgtcctgtc atccttatcc acctgagcaa cctcaccggc    420

ctgagcaacg actacagcag gagaaccatg ggactccttg tctcagacat cgggactatc    480

gtgtgggggg ctaccagcgc catggcaacc ggctatgtta aagtcatctt cttttgtctt    540

ggattgtgct atggcgcgaa cacatttttt cacgccgcca aagcatatat cgagggttat    600

catactgtgc caaagggtcg gtgccgccag gtcgtgaccg gcatggcatg gctgtttttc    660

gtgagctggg gtatgttccc aattctcttc attttggggc ccgaaggttt tggcgtcctg    720

agcgtctatg gctccaccgt aggtcacacg attattgatc tgatgagtaa aaattgttgg    780

gggttgttgg gacactacct gcgcgtcctg atccacgagc acatattgat tcacggagat    840

atccgcaaaa ccaccaaact gaacatcggc ggaacggaga tcgaggtcga gactctcgtc    900

gaagacgaag ccgaggccgg agccgtgcca gcggccgcca ccatggtgag caagggcgag    960

gagctgttca ccggggtggt gcccatcctg gtcgagctgg acggcgacgt aaacggccac   1020

aagttcagcg tgtccggcga gggcgagggc gatgccacct acggcaagct gaccctgaag   1080

ttcatctgca ccaccggcaa gctgcccgtg ccctggccca ccctcgtgac caccttcggc   1140

tacggcctgc agtgcttcgc ccgctacccc gaccacatga agcagcacga cttcttcaag   1200

tccgccatgc ccgaaggcta cgtccaggag cgcaccatct tcttcaagga cgacggcaac   1260

tacaagaccc gcgccgaggt gaagttcgag ggcgacaccc tggtgaaccg catcgagctg   1320

aagggcatcg acttcaagga ggacggcaac atcctggggc acaagctgga gtacaactac   1380

aacagccaca acgtctatat catggccgac aagcagaaga acggcatcaa ggtgaacttc   1440

aagatccgcc acaacatcga ggacggcagc gtgcagctcg ccgaccacta ccagcagaac   1500

acccccatcg gcgacggccc cgtgctgctg cccgacaacc actacctgag ctaccagtcc   1560

gccctgagca aagaccccaa cgagaagcgc gatcacatgg tcctgctgga gttcgtgacc   1620

gccgccggga tcactctcgg catggacgag ctgtacaagg gatccggagc tactaacttc   1680

agcctgctga agcaggctgg agacgtggag gagaaccctg gacctactag tatgggcagc   1740

gtgaagctga tccccagcct gaccaccgtg atcctcgtga agtccatgct gcggaagcgg   1800
```

```
agcttcggca accccttcaa gtataatacg gagaccctgt accccgctga cggcggcctg   1860

gaaggcgcat gtgacatggc cctgaagctc gtgggcgggg gccacctgaa ctgcagcctt   1920

gagaccacat acagatccaa gaaacccgct acgaacctca agatgcccgg tgtctacaac   1980

gtggaccaca gactggaacg aatcaaagag gccgacgatg agacctacgt cgagctgcac   2040

gaggtggctg tggccagata cgtgggcctg ggtggtggcg gaggtacagg cgggagtgtg   2100

agcgagctga ttaaggagaa catgccaatg aagctgtaca tggagggcac cgtgaacaac   2160

caccacttca agtgcacatc cgagggcgaa ggcaagccct acgagggcac ccagaccatg   2220

agaatcaagg tcgtcgaggg cggccctctc cccttcgcct tcgacatcct ggctaccagc   2280

ttcatgtacg gcagcagaac cttcatcaag caccctcctg gcatccccga cttctttaag   2340

cagtccttcc ctgagggctt cacatgggag agagtcacca catacgaaga cgggggcgtg   2400

ctgaccgcta cccaggacac cagcctccag gacggctgcc tcatctacaa cgtcaaggtt   2460

agagggatga acttcccagc caacggccct gtgatgcaga agaaaacact cggctgggag   2520

gccagtaatg gccaactgac tgaagagcag atcgcagaat ttaaagaggc tttctcccta   2580

tttgacaagg acggggatgg gacgataaca accaaggagc tggggacggt gatgcggtct   2640

ctggggcaga accccacaga agcggagctg caggacatga tcaatgaagt agatgccgac   2700

ggtgacggca cattcgactt ccctgagttc ctgacgatga tggcaagaaa aatgagttat   2760

agagtcactg aagaggaaat tagagaagcg ttccgcgtgt ttgataagga cggcaatggc   2820

tacatcggcg cagcagagct tcgccacgtg atgacagacc ttggagagaa gttaacagat   2880

gaggaggttg atgaaatgat cagggtagca gacatcgatg gggatggtca ggtaaactac   2940

gaagagtttg tacaaatgat gacagcgaag tag                                2973
```

<210> SEQ ID NO 3
<211> LENGTH: 1488
<212> TYPE: DNA
<213> ORGANISM: Artificial Sequence
<220> FEATURE:
<223> OTHER INFORMATION: Artificial sequence based on bacterial sequence

<400> SEQUENCE: 3

```
atgtcggtac cgctgactac ctcagcattc ggccacgcgt ttctggctaa ctgtgaacgt     60

gagcagatcc acctggcggg ctccattcag ccgcacggta tcctgctggc tgttaaagag    120

cctgacaacg tggtgatcca ggcttctatt aacgctgcgg agttcctgaa caccaacttt    180

gttgttggcc gtccgctgcg tgacctgggc ggcgatctgc ctttgcagat cctgccgcac    240

ctgaacggcc cgctgcacct ggctccgatg accctgcgtt gtactgtggg ttctccgccg    300

cgtcgtgtgg actgtaccat tcatcgtccg tctaacggcg gcctgatcgt agaactggaa    360

ccagcaacca aggccactaa cattgcgccg gctctggtcg gtgcgcttca tcgtatcact    420

tcttcatcct ccctgatggg cctgtgtgac gaaaccgcga ctattttccg tgagattact    480

ggcttcgacc gtgtgatggt aatgcgtctc ggcgcgcttg acgatctgac tgaagagcag    540

atcgcagaga ttaaagaggc tttctcccta tttgacaagg acggggacgg gacgataaca    600

accaaggagc tggggacggt gttccggtct ctggggcaga accccacaga agcagagctg    660

caggacatga tcaatgaagt agatgccgat ggcgacggca cattcgactt ccctgagttc    720

ctgacgatga tggcaaggaa aatgaatgac tcagacagtg aagaggaaat tagagaagcg    780

ttccgcgtgt ttgataagga cggcaatggc tacatcggcg cagcagagct tcgccacgtg    840
```

-continued

```
atgacagacc ttggtgagaa gttaactgat gaggaggttg atgaaatgat cagggtagca      900

gacaacgatg gggatggtca ggtaaactac gaagagtttg tacaaatgat gacagcgaag      960

ggtggcggag gttctgtaga ttcatcacgt cgtaagtgga ataaggcagg tcacgcagtc     1020

agagctatag gtcggctgag ctcgcgtagg catgatttgc tgtccgaatg tcgtcgtgcg     1080

gacctggaag cgttcctggg taaccgctac ccggcgtcta ctattccgca gatcgctcgt     1140

cgcctgtacg aacttaaccg tgttcgcctg ctggtagatg tgaactatac tccggttccg     1200

ctacagccgc gcatcagccc gctgaacggt cgtgatctgg atatgtccct gtcttgcctg     1260

cgctctatgt ccccgatcca ccagaaatac atgcaggaca tgggcgttgg cgcaaccctg     1320

gtttgctctc tgatggtgtc tggtcgtctg tggggtctga tcgtttgcca ccactacgaa     1380

ccgcgcttcg ttccgtccca cattcgcgct gctggcgaag cgctggcgga aacttgtgcg     1440

aaccgcatcg cgacgctgga gagctttgca cagtctcagt ccaaatga                  1488
```

```
<210> SEQ ID NO 4
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 4

atgtcggtac cgctgactac ctcagcattc ggccacgcgt ttctggctaa ctgtgaacgt       60

gagcagatcc acctggcggg ctccattcag ccgcacggta tcctgctggc tgttaaagag      120

cctgacaacg tggtgatcca ggcttctatt aacgctgcgg agttcctgaa caccaacttt      180

gttgttggcc gtccgctgcg tgacctgggc ggcgatctgc ctttgcagat cctgccgcac      240

ctgaacggcc cgctgcacct ggctccgatg accctgcgtt gtactgtggg ttctccgccg      300

cgtcgtgtgg actgtaccat tcatcgaccg tctaacggcg gcctgatcgt agaactggaa      360

ccagcaacca aggccactaa cattgcgccg gctctggtcg gtgcgcttca tcgtatcact      420

tcttcatcct ccctgatggg cctgtgtgac gaaaccgcga ctattttccg tgagattact      480

ggtttcgacc gtgtgatggt aatgcgtctc ggcgcgcttg acgatctgac tgaagagcag      540

atcgcagaga ttaaagaggc tttctcccta tttgacaagg acggggacgg gacgataaca      600

accaaggagc tggggacggt gttccggtct ctggggcaga accccacaga agcagagctg      660

caggacatga tcaatgaagt agatgccgat ggcgacggca tattcgactt ccctgagttc      720

ctgacgatga tggcaaggaa aatgaatgac tcagacagtg aagaggaaat tagaggagcg      780

ttccgcgtgt ttgataagga cggcaatggc tacatcggcg cagcagagct tcgccacgtg      840

atgacagacc ttggtgagaa gttaactgat gaggaggttg atgaaatgat cagggtagca      900

gacaacgatg gggatggtca ggtaaactac gaagagtttg tacaaatgat gacagcgaag      960

ggtggcggag gttctgtaga ttcatcacgt cgtaagtgga ataaggcagg tcacgcagtc     1020

agagctatag gtcggctggg ctcgcgtagg catgatttgc tgtccgaatg tcgtcgtgcg     1080

gacctggaag cgttcctagg taaccgctac ccggcgtcta ctattccgca gatcgctcgt     1140

cgcctgtacg aactcaaccg tgttcgcctg ctggtagatg tgaactatac tccggttccg     1200

ctagagccgc gcatcagccc gctgaacggt cgtgatctgg atatgtccct gtcttgcctg     1260

cgctctatgt ccccgatcca ccagaaatac atgcaggaca tgggcgttgg cgcaaccctg     1320

gtttgctctc tgatggtgtc tggtcgtctg tggggtctga tcgtttgcca ccactacgaa     1380

ccgcgctacg ttccgtccca cattcgcgct gctggcgaag cgctggcgga agcatgtgcg     1440
```

aaccgcatcg cgacgctgga gagctttgca cagtctcagt ccaaa 1485

<210> SEQ ID NO 5
<211> LENGTH: 413
<212> TYPE: PRT
<213> ORGANISM: Artificial Sequence
<220> FEATURE:
<223> OTHER INFORMATION: Artificial sequence based on bacterial sequence

<400> SEQUENCE: 5

```
Met Gly Ser Val Lys Leu Ile Pro Ser Leu Thr Thr Val Ile Leu Val
1               5                   10                  15

Lys Ser Met Leu Arg Lys Arg Ser Phe Gly Asn Pro Phe Lys Tyr Asn
            20                  25                  30

Thr Glu Thr Leu Tyr Pro Ala Asp Gly Gly Leu Glu Gly Ala Cys Asp
        35                  40                  45

Met Ala Leu Lys Leu Val Gly Gly Gly His Leu Asn Cys Ser Leu Glu
    50                  55                  60

Thr Thr Tyr Arg Ser Lys Lys Pro Ala Thr Asn Leu Lys Met Pro Gly
65                  70                  75                  80

Val Tyr Asn Val Asp His Arg Leu Glu Arg Ile Lys Glu Ala Asp Asp
                85                  90                  95

Glu Thr Tyr Val Glu Leu His Glu Val Ala Val Ala Arg Tyr Val Gly
            100                 105                 110

Leu Gly Gly Gly Gly Gly Thr Gly Gly Ser Val Ser Glu Leu Ile Lys
        115                 120                 125

Glu Asn Met Pro Met Lys Leu Tyr Met Glu Gly Thr Val Asn Asn His
    130                 135                 140

His Phe Lys Cys Thr Ser Glu Gly Glu Gly Lys Pro Tyr Glu Gly Thr
145                 150                 155                 160

Gln Thr Met Arg Ile Lys Val Val Glu Gly Gly Pro Leu Pro Phe Ala
                165                 170                 175

Phe Asp Ile Leu Ala Thr Ser Phe Met Tyr Gly Ser Arg Thr Phe Ile
            180                 185                 190

Lys His Pro Pro Gly Ile Pro Asp Phe Phe Lys Gln Ser Phe Pro Glu
        195                 200                 205

Gly Phe Thr Trp Glu Arg Val Thr Thr Tyr Glu Asp Gly Gly Val Leu
    210                 215                 220

Thr Ala Thr Gln Asp Thr Ser Leu Gln Asp Gly Cys Leu Ile Tyr Asn
225                 230                 235                 240

Val Lys Val Arg Gly Met Asn Phe Pro Ala Asn Gly Pro Val Met Gln
                245                 250                 255

Lys Lys Thr Leu Gly Trp Glu Ala Ser Asn Gly Gln Leu Thr Glu Glu
            260                 265                 270

Gln Ile Ala Glu Phe Lys Glu Ala Phe Ser Leu Phe Asp Lys Asp Gly
        275                 280                 285

Asp Gly Thr Ile Thr Thr Lys Glu Leu Gly Thr Val Met Arg Ser Leu
    290                 295                 300

Gly Gln Asn Pro Thr Glu Ala Glu Leu Gln Asp Met Ile Asn Glu Val
305                 310                 315                 320

Asp Ala Asp Gly Asp Gly Thr Phe Asp Phe Pro Glu Phe Leu Thr Met
                325                 330                 335

Met Ala Arg Lys Met Ser Tyr Arg Val Thr Glu Glu Glu Ile Arg Glu
            340                 345                 350
```

-continued

```
Ala Phe Arg Val Phe Asp Lys Asp Gly Asn Gly Tyr Ile Gly Ala Ala
        355                 360                 365

Glu Leu Arg His Val Met Thr Asp Leu Gly Glu Lys Leu Thr Asp Glu
    370                 375                 380

Glu Val Asp Glu Met Ile Arg Val Ala Asp Ile Asp Gly Asp Gly Gln
385                 390                 395                 400

Val Asn Tyr Glu Glu Phe Val Gln Met Met Thr Ala Lys
                405                 410
```

<210> SEQ ID NO 6
<211> LENGTH: 495
<212> TYPE: PRT
<213> ORGANISM: Artificial Sequence
<220> FEATURE:
<223> OTHER INFORMATION: Artificial sequence based on bacterial sequence

<400> SEQUENCE: 6

```
Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Phe Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Ala Thr Asn Ile
        115                 120                 125

Ala Pro Ala Leu Val Gly Ala Leu His Arg Ile Thr Ser Ser Ser Ser
    130                 135                 140

Leu Met Gly Leu Cys Asp Glu Thr Ala Thr Ile Phe Arg Glu Ile Thr
145                 150                 155                 160

Gly Phe Asp Arg Val Met Val Met Arg Leu Gly Ala Leu Asp Asp Leu
                165                 170                 175

Thr Glu Glu Gln Ile Ala Glu Ile Lys Glu Ala Phe Ser Leu Phe Asp
            180                 185                 190

Lys Asp Gly Asp Gly Thr Ile Thr Thr Lys Glu Leu Gly Thr Val Phe
        195                 200                 205

Arg Ser Leu Gly Gln Asn Pro Thr Glu Ala Glu Leu Gln Asp Met Ile
    210                 215                 220

Asn Glu Val Asp Ala Asp Gly Asp Gly Thr Phe Asp Phe Pro Glu Phe
225                 230                 235                 240

Leu Thr Met Met Ala Arg Lys Met Asn Asp Ser Asp Ser Glu Glu Glu
                245                 250                 255

Ile Arg Glu Ala Phe Arg Val Phe Asp Lys Asp Gly Asn Gly Tyr Ile
            260                 265                 270

Gly Ala Ala Glu Leu Arg His Val Met Thr Asp Leu Gly Glu Lys Leu
        275                 280                 285

Thr Asp Glu Glu Val Asp Glu Met Ile Arg Val Ala Asp Asn Asp Gly
    290                 295                 300
```

-continued

```
Asp Gly Gln Val Asn Tyr Glu Glu Phe Val Gln Met Met Thr Ala Lys
305                 310                 315                 320

Gly Gly Gly Gly Ser Val Asp Ser Ser Arg Arg Lys Trp Asn Lys Ala
                325                 330                 335

Gly His Ala Val Arg Ala Ile Gly Arg Leu Ser Ser Arg Arg His Asp
            340                 345                 350

Leu Leu Ser Glu Cys Arg Arg Ala Asp Leu Glu Ala Phe Leu Gly Asn
        355                 360                 365

Arg Tyr Pro Ala Ser Thr Ile Pro Gln Ile Ala Arg Arg Leu Tyr Glu
    370                 375                 380

Leu Asn Arg Val Arg Leu Leu Val Asp Val Asn Tyr Thr Pro Val Pro
385                 390                 395                 400

Leu Gln Pro Arg Ile Ser Pro Leu Asn Gly Arg Asp Leu Asp Met Ser
                405                 410                 415

Leu Ser Cys Leu Arg Ser Met Ser Pro Ile His Gln Lys Tyr Met Gln
            420                 425                 430

Asp Met Gly Val Gly Ala Thr Leu Val Cys Ser Leu Met Val Ser Gly
        435                 440                 445

Arg Leu Trp Gly Leu Ile Val Cys His His Tyr Glu Pro Arg Phe Val
    450                 455                 460

Pro Ser His Ile Arg Ala Ala Gly Glu Ala Leu Ala Glu Thr Cys Ala
465                 470                 475                 480

Asn Arg Ile Ala Thr Leu Glu Ser Phe Ala Gln Ser Gln Ser Lys
                485                 490                 495


<210> SEQ ID NO 7
<211> LENGTH: 495
<212> TYPE: PRT
<213> ORGANISM: Artificial Sequence
<220> FEATURE:
<223> OTHER INFORMATION: Artificial sequence based on bacterial sequence

<400> SEQUENCE: 7

Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Phe Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Ala Thr Asn Ile
        115                 120                 125

Ala Pro Ala Leu Val Gly Ala Leu His Arg Ile Thr Ser Ser Ser Ser
    130                 135                 140

Leu Met Gly Leu Cys Asp Glu Thr Ala Thr Ile Phe Arg Glu Ile Thr
145                 150                 155                 160

Gly Phe Asp Arg Val Met Val Met Arg Leu Gly Ala Leu Asp Asp Leu
                165                 170                 175
```

-continued

```
Thr Glu Glu Gln Ile Ala Glu Ile Lys Glu Ala Phe Ser Leu Phe Asp
            180                 185                 190

Lys Asp Gly Asp Gly Thr Ile Thr Thr Lys Glu Leu Gly Thr Val Phe
        195                 200                 205

Arg Ser Leu Gly Gln Asn Pro Thr Glu Ala Glu Leu Gln Asp Met Ile
    210                 215                 220

Asn Glu Val Asp Ala Asp Gly Asp Gly Ile Phe Asp Phe Pro Glu Phe
225                 230                 235                 240

Leu Thr Met Met Ala Arg Lys Met Asn Asp Ser Asp Ser Glu Glu Glu
                245                 250                 255

Ile Arg Gly Ala Phe Arg Val Phe Asp Lys Asp Gly Asn Gly Tyr Ile
            260                 265                 270

Gly Ala Ala Glu Leu Arg His Val Met Thr Asp Leu Gly Glu Lys Leu
        275                 280                 285

Thr Asp Glu Glu Val Asp Glu Met Ile Arg Val Ala Asp Asn Asp Gly
    290                 295                 300

Asp Gly Gln Val Asn Tyr Glu Glu Phe Val Gln Met Met Thr Ala Lys
305                 310                 315                 320

Gly Gly Gly Gly Ser Val Asp Ser Ser Arg Arg Lys Trp Asn Lys Ala
                325                 330                 335

Gly His Ala Val Arg Ala Ile Gly Arg Leu Gly Ser Arg Arg His Asp
            340                 345                 350

Leu Leu Ser Glu Cys Arg Arg Ala Asp Leu Glu Ala Phe Leu Gly Asn
        355                 360                 365

Arg Tyr Pro Ala Ser Thr Ile Pro Gln Ile Ala Arg Arg Leu Tyr Glu
    370                 375                 380

Leu Asn Arg Val Arg Leu Leu Val Asp Val Asn Tyr Thr Pro Val Pro
385                 390                 395                 400

Leu Glu Pro Arg Ile Ser Pro Leu Asn Gly Arg Asp Leu Asp Met Ser
                405                 410                 415

Leu Ser Cys Leu Arg Ser Met Ser Pro Ile His Gln Lys Tyr Met Gln
            420                 425                 430

Asp Met Gly Val Gly Ala Thr Leu Val Cys Ser Leu Met Val Ser Gly
        435                 440                 445

Arg Leu Trp Gly Leu Ile Val Cys His His Tyr Glu Pro Arg Tyr Val
    450                 455                 460

Pro Ser His Ile Arg Ala Ala Gly Glu Ala Leu Ala Glu Ala Cys Ala
465                 470                 475                 480

Asn Arg Ile Ala Thr Leu Glu Ser Phe Ala Gln Ser Gln Ser Lys
                485                 490                 495
```